(12) United States Patent
Hodge et al.

(10) Patent No.: US 7,605,181 B2
(45) Date of Patent: Oct. 20, 2009

(54) METHOD FOR THE TREATMENT OF METABOLIC DISORDERS

(75) Inventors: Kirvin L. Hodge, Laurel, MD (US); Shalini Sharma, Gaithersburg, MD (US); Albert C. Lee, St. Louis, MO (US); Reid W. von Borstel, Potomac, MD (US)

(73) Assignee: Wellstat Therapeutics Orporation, Gaithersburg, MD (US)

( * ) Notice: Subject to any disclaimer, the term of this patent is extended or adjusted under 35 U.S.C. 154(b) by 0 days.

(21) Appl. No.: 11/841,489

(22) Filed: Aug. 20, 2007

(65) Prior Publication Data

US 2008/0015254 A1 Jan. 17, 2008

Related U.S. Application Data

(63) Continuation of application No. 10/531,630, filed as application No. PCT/US2004/003718 on Feb. 9, 2004.

(60) Provisional application No. 60/447,168, filed on Feb. 13, 2003.

(51) Int. Cl.
*A61K 31/515* (2006.01)
(52) U.S. Cl. .................................... 514/570
(58) Field of Classification Search .................. 514/570
See application file for complete search history.

(56) References Cited

U.S. PATENT DOCUMENTS

| | | | |
|---|---|---|---|
| 3,976,673 A | 8/1976 | Pifferi | |
| 4,098,816 A | 7/1978 | Thorne et al. | |
| 4,268,442 A | 5/1981 | Kondo et al. | |
| 4,897,397 A | 1/1990 | Shih et al. | |
| 4,939,171 A | 7/1990 | Moeller et al. | |
| 5,589,492 A * | 12/1996 | Haigh | 514/339 |
| 6,858,602 B2 | 2/2005 | Sharma et al. | |
| 6,916,848 B2 | 7/2005 | Sharma | |
| 6,924,314 B2 | 8/2005 | Sharma et al. | |
| 6,946,491 B2 | 9/2005 | Sharma et al. | |
| 7,012,071 B2 | 3/2006 | Sharma et al. | |
| 7,041,659 B2 | 5/2006 | Sharma | |
| 7,045,541 B2 | 5/2006 | Sharma | |
| 7,101,910 B2 | 9/2006 | Sharma | |
| 2003/0191323 A1 | 10/2003 | Ikawa et al. | |
| 2004/0214901 A1 | 10/2004 | Antel et al. | |
| 2005/0090555 A1 | 4/2005 | Sharma et al. | |
| 2005/0256333 A1 | 11/2005 | Sharma et al. | |
| 2006/0014784 A1 | 1/2006 | Hodge et al. | |
| 2006/0035970 A1 | 2/2006 | Hodge et al. | |
| 2006/0247309 A1 | 11/2006 | Hodge et al. | |
| 2007/0105955 A1 | 5/2007 | Hodge et al. | |
| 2007/0105958 A1 | 5/2007 | Sharma et al. | |
| 2007/0173544 A1 | 7/2007 | Hodge et al. | |
| 2007/0249696 A1 | 10/2007 | Sharma et al. | |
| 2007/0249719 A1 | 10/2007 | Sharma et al. | |
| 2007/0265322 A1 | 11/2007 | Sharma et al. | |
| 2007/0282003 A1 | 12/2007 | Sharma et al. | |
| 2008/0015209 A1 | 1/2008 | Sharma et al. | |
| 2008/0021109 A1 | 1/2008 | Sharma et al. | |
| 2008/0027229 A1 | 1/2008 | Hodge et al. | |

FOREIGN PATENT DOCUMENTS

| | | |
|---|---|---|
| EP | 1099701 A1 | 5/2001 |
| EP | 1300142 A1 | 4/2003 |
| EP | 1593667 A1 | 11/2005 |

(Continued)

OTHER PUBLICATIONS

Kuchar, et al., "Substituted Benzyloxyarylacetic Acids:Synthesis and Quantitative Relationships Between Structure and Antiinflammatory Activity", Collection Czech. Chem. Commun., vol. 42, pp. 1723-1735, 1977.
Katou, et al., Japanese Patent Application No. 01-216961, published Aug. 30, 1989. (Abstract).
Nakagawa, et al., Japanese Patent Application No. 03-048603, published Mar. 1, 1991. (Abstract).
Lewis, Sr., "Hawley's Condensed Chemical Dictionary", Fourteenth Edition, John Wiley & Sons, Inc., p. 206, 2001.

(Continued)

*Primary Examiner*—Deborah D Carr
(74) *Attorney, Agent, or Firm*—Lewis J. Kreisler

(57) ABSTRACT

Agents useful for the treatment of various metabolic disorders, such as insulin resistance syndrome, diabetes, hyperlipidemia, fatty liver disease, cachexia, obesity, atherosclerosis and arteriosclerosis are disclosed.

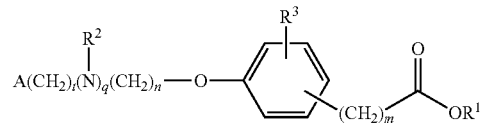

Formula I wherein n is 1 or 2; m is 0, 1, 2, 4, or 5; q is 0 or 1; t is 0 or 1; $R^2$ is alkyl having from 1 to 3 carbon atoms; $R^3$ is hydrogen, halo, alkyl having from 1 to 3 carbon atoms, or alkoxy having from 1 to 3 carbon atoms;

A is phenyl, unsubstituted or substituted by 1 or 2 groups selected from: halo, alkyl having 1 or 2 carbon atoms, perfluoromethyl, alkoxy having 1 or 2 carbon atoms, and perfluoromethoxy; or cycloalkyl having from 3 to 6 ring carbon atoms wherein the cycloalkyl is unsubstituted or one or two ring carbons are independently mono-substituted by methyl or ethyl; or a 5 or 6 membered heteroaromatic ring having 1 or 2 ring heteroatoms selected from N, S and O and the heteroaromatic ring is covalently bound to the remainder of the compound of formula I by a ring carbon; and $R^1$ is hydrogen or alkyl having 1 or 2 carbon atoms. Alternatively, when $R^1$ is hydrogen, the biologically active agent can be a pharmaceutically acceptable salt of the compound of Formula I.

7 Claims, No Drawings

FOREIGN PATENT DOCUMENTS

| | | | |
|---|---|---|---|
| JP | 01-216961 | | 8/1989 |
| JP | 03-048603 | | 3/1991 |
| JP | 08325250 | * | 12/1996 |
| WO | 94/05153 A1 | | 3/1994 |
| WO | 95/20578 A1 | | 8/1995 |
| WO | 98/03505 A1 | | 1/1998 |
| WO | 98/10763 A1 | | 3/1998 |
| WO | 99/11255 A1 | | 3/1999 |
| WO | WO9911255 | * | 3/1999 |
| WO | 99/19291 A1 | | 4/1999 |
| WO | 99/54284 A1 | | 10/1999 |
| WO | 01/60813 A1 | | 8/2001 |
| WO | 02/100341 A2 | | 12/2002 |
| WO | WO02100341 | * | 12/2002 |
| WO | 2005/019151 A1 | | 3/2005 |

OTHER PUBLICATIONS

Wedick, et al. "Insulin resistance precedes weight loss in adults without diabetes: The Rancho Bernardo Study", American Journal of Epidemiology, 153(12), pp. 1199-1205, 2001. (Abstract).

Rofe, et al., "Altered insulin response to glucose in weight-losing cancer patients", Anticancer Research, 14(2B), pp. 647-650, 1994. (Abstract).

Tayek, "A review of cancer cachexia and abnormal glucose metabolism in humans with cancer", Journal of the American College of Nutrition, 11(4), pp. 445-456, 1992. (Abstract).

Argiles, et al., "Journey from cachexia to obesity by TNF", the FASEB Journal, 11(10), pp. 743-751, 1997. (Abstract).

de Alvaro, et al., "Tumor necrosis factor alpha produces insulin resistance in skeletal muscle by activation of inhibitor kappaB kinase in a p38 MAPK-dependent manner", Journal of Biol Chem., 279(17), pp. 17070-17078, 2004. (Abstract).

Jones, "Halogenation of Phenolic Ethers and Anilides. Part XIV m-Substituted Phenyl Esthers", Journal of the Chemical Society, pp. 430-432, 1943. XP00807474.

Kuchar, et al., "Synthesis of arylacetic acid and their effect on activation of fibrinolysis. Quantitative relations between structure and biological activity", Collection of Czechoslovak Chemical Communications, 45(5), pp. 1401-1409, 1980. XP-002418932.

Orr, et al., "Improved synthesis of 5-benzyl-2-thiouracils", Synthetic Communications, 26(1), pp. 179-189, 1996. XP-002418933.

Buu, et al., "Antiinflammatory and analgesic arylacethydroxamic acids", Chim. Ther., 2(1), pp. 39-48, 1967. XP-002418934.

Kuchar, et al., "The synthesis of arylpropionic acids and the quantitative relationship between the structure and the activation of fibrinolysis", Collection of Czechoslovak Chemical Communications, 46(5), pp. 1173-1187, 1981. XP-002418936.

Kuchar, et al., "Relationships between gas-liquid chromatographic behavior and structure of aryl-aliphatic acid", Journal of Chromatograph, 333(1), pp. 21-28, 1985. XP-002418937.

Davies, et al., "Asymmetric Intramolecular C-H Insertions of Aryldiazoacetates", Organic Letters, 3(10), 1475-1477, 2001. XP-002418938.

Coates, et al., "Cyclic nucleotide phosphodiesterase inhibition by imidazopyridines: analogs of sulmazole and isomazole as inhibitors of the cGMP specific phosphodiesterase", Journal of Medicinal Chemistry, 36(10), 1387-1392, 1993. XP-002418940.

Maercker, "Cleavage of cyclopropylcarbinyl phenyl ether by alkali metals", Justus Liebigs Annalen der Chemie, 730, pp. 91-99, 1969. XP-002418941.

Chemical abstract DN 95:150228, also cited as ES488558. XP-002418935.

Chemical abstract DN 139:214465, also cited as WO03070686. XP-002418942.

Chemical abstract DN 141:71356, also cited as WO04052839. XP-002418943.

Chemical abstract DN:142:279952, also cited as WO05016862. XP-002418944.

Chemical Abstract DN:128:154084, corresponding to Momose, et al. WO98/03505 (1998). See compound RN152380-68-2.

Chemical Abstract DN: 130: 237567, corresponding to Tajima, et al. WO99/11255 (1999). See compounds RN 221258-65-7, 221258-68-0 and 221261-93-4.

Chemical Abstract DN: 130:281874, corresponding to Shoda, et al. WO99/19291 (1999). See compounds RN 222627-31-8 and 222627-32-9.

Chemical Abstract DN: 65:20620, corresponding to Carlo, BE 667498 (1965). See compounds RN 6686-26-6.

Pending (as of Mar. 24, 2008) claims from U.S. Appl. No. 11/772,515.

Pending (as of Mar. 24, 2008) claims from U.S. Appl. No. 11/772,520.

Pending (as of Mar. 24, 2008) claims from U.S. Appl. No. 11/772,560.

Pending (as of Sep. 19, 2007) claims from U.S. Appl. No. 11/909,120.

Faller, "A new solvatochromic chelating agent", Analytica Chimica Acta, 32(6), 586-9, 1965. Compound having Chemical Abstract RN 186-58-8.

Compound having Chemical Abstract RN 6388-94-9, registered before 2001.

Compound having Chemical Abstract RN 6547-53-1. (known from DE 3017499).

Compound having Chemical Abstract RN 22047-88-7, (known from EP 11279).

Compound having Chemical Abstract RN 64360-35-6, registered before 2001.

Compound having Chemical Abstract RN 76968-92-8, registered before 2001.

Compound having Chemical Abstract RN 136137-46-7, registered before 2001.

Compound having Chemical Abstract RN 125721-53-1, registered before 2001.

Compound having Chemical Abstract RN 64360-38-9, registered before 2001.

Compound having Chemical Abstract RN 130604-43-2, registered before 2001.

Compound having Chemical Abstract RN 56441-69-1, registered before 2001.

Compound having Chemical Abstract RN 56441-95-3, registered before 2001.

Compound having Chemical Abstract RN 56441-70-4, registered before 2001.

Compound having Chemical Abstract RN 56441-92-0, registered before 2001.

Compound having Chemical Abstract RN 56441-93-1, registered before 2001.

Compound having Chemical Abstract RN 56441-94-2, registered before 2001.

Compound having Chemical Abstract RN 56441-96-4, registered before 2001.

Compound having Chemical Abstract RN 56442-29-6, registered before 2001.

* cited by examiner

METHOD FOR THE TREATMENT OF METABOLIC DISORDERS

BACKGROUND OF THE INVENTION

Diabetes mellitus is a major cause of morbidity and mortality. Chronically elevated blood glucose leads to debilitating complications: nephropathy, often necessitating dialysis or renal transplant; peripheral neuropathy; retinopathy leading to blindness; ulceration of the legs and feet, leading to amputation; fatty liver disease, sometimes progressing to cirrhosis; and vulnerability to coronary artery disease and myocardial infarction.

There are two primary types of diabetes. Type I, or insulin-dependent diabetes mellitus (IDDM) is due to autoimmune destruction of insulin-producing beta cells in the pancreatic islets. The onset of this disease is usually in childhood or adolescence. Treatment consists primarily of multiple daily injections of insulin, combined with frequent testing of blood glucose levels to guide adjustment of insulin doses, because excess insulin can cause hypoglycemia and consequent impairment of brain and other functions.

Type II, or noninsulin-dependent diabetes mellitus (NIDDM) typically develops in adulthood. NIDDM is associated with resistance of glucose-utilizing tissues like adipose tissue, muscle, and liver, to the actions of insulin. Initially, the pancreatic islet beta cells compensate by secreting excess insulin. Eventual islet failure results in decompensation and chronic hyperglycemia. Conversely, moderate islet insufficiency can precede or coincide with peripheral insulin resistance. There are several classes of drugs that are useful for treatment of NIDDM: 1) insulin releasers, which directly stimulate insulin release, carrying the risk of hypoglycemia; 2) prandial insulin releasers, which potentiate glucose-induced insulin secretion, and must be taken before each meal; 3) biguanides, including metformin, which attenuate hepatic gluconeogenesis (which is paradoxically elevated in diabetes); 4) insulin sensitizers, for example the thiazolidinedione derivatives rosiglitazone and pioglitazone, which improve peripheral responsiveness to insulin, but which have side effects like weight gain, edema, and occasional liver toxicity; 5) insulin injections, which are often necessary in the later stages of NIDDM when the islets have failed under chronic hyperstimulation.

Insulin resistance can also occur without marked hyperglycemia, and is generally associated with atherosclerosis, obesity, hyperlipidemia, and essential hypertension. This cluster of abnormalities constitutes the "metabolic syndrome" or "insulin resistance syndrome". Insulin resistance is also associated with fatty liver, which can progress to chronic inflammation (NASH; "nonalcoholic steatohepatitis"), fibrosis, and cirrhosis. Cumulatively, insulin resistance syndromes, including but not limited to diabetes, underlie many of the major causes of morbidity and death of people over age 40.

Despite the existence of such drugs, diabetes remains a major and growing public health problem. Late stage complications of diabetes consume a large proportion of national health care resources. There is a need for new orally active therapeutic agents which effectively address the primary defects of insulin resistance and islet failure with fewer or milder side effects than existing drugs.

Currently there are no safe and effective treatments for fatty liver disease. Therefore such a treatment would be of value in treating this condition.

WO 02/100341 (Wellstat Therapeutics Corp.) discloses 4-(3-2,6-Dimethylbenzyloxy)phenyl)butyric acid. WO 02/100341 does not disclose any compounds within the scope of Formula I shown below, in which m is 0, 1, 2, 4, or 5.

SUMMARY OF THE INVENTION

This invention provides a biologically active agent as described below. This invention provides the use of the biologically active agent described below in the manufacture of a medicament for the treatment of insulin resistance syndrome, diabetes, cachexia, hyperlipidemia, fatty liver disease, obesity, atherosclerosis or arteriosclerosis. This invention provides methods of treating a mammalian subject with insulin resistance syndrome, diabetes, cachexia, hyperlipidemia, fatty liver disease, obesity, atherosclerosis or arteriosclerosis comprising administering to the subject an effective amount of the biologically active agent described below. This invention provides a pharmaceutical composition comprising the biologically active agent described below and a pharmaceutically acceptable carrier.

The biologically active agent in accordance with this invention is a compound of Formula I:

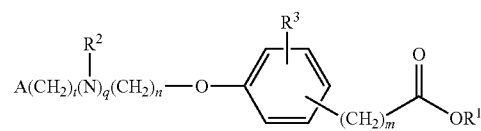

Formula I wherein n is 1 or 2; m is 0, 1, 2, 4 or 5; q is 0 or 1; t is or 1; $R^2$ is alkyl having from 1 to 3 carbon atoms; $R^3$ is hydrogen, halo, alkyl having from 1 to 3 carbon atoms, or alkoxy having from 1 to 3 carbon atoms;

A is phenyl, unsubstituted or substituted by 1 or 2 groups selected from: halo, alkyl having 1 or 2 carbon atoms, perfluoromethyl, alkoxy having 1 or 2 carbon atoms, and perfluoromethoxy; or cycloalkyl having from 3 to 6 ring carbon atoms wherein the cycloalkyl is unsubstituted or one or two ring carbons are independently mono-substituted by methyl or ethyl; or a 5 or 6 membered heteroaromatic ring having 1 or 2 ring heteroatoms selected from N, S and O and the heteroaromatic ring is covalently bound to the remainder of the compound of formula I by a ring carbon; and $R^1$ is hydrogen or alkyl having 1 or 2 carbon atoms. Alternatively, when $R^1$ is hydrogen, the biologically active agent can be a pharmaceutically acceptable salt of the compound of Formula I.

The biologically active agents described above have activity in one or more of the biological activity assays described below, which are established animal models of human diabetes and insulin resistance syndrome. Therefore such agents would be useful in the treatment of diabetes and insulin resistance syndrome. All of the exemplified compounds that were tested demonstrated activity in at least one of the biological activity assays in which they were tested.

DETAILED DESCRIPTION OF THE INVENTION

Definitions

As used herein the term "alkyl" means a linear or branched-chain alkyl group. An alkyl group identified as having a certain number of carbon atoms means any alkyl group having the specified number of carbons. For example, an alkyl having three carbon atoms can be propyl or isopropyl; and alkyl having four carbon atoms can be n-butyl, 1-methylpropyl, 2-methylpropyl or t-butyl.

As used herein the term "halo" refers to one or more of fluoro, chloro, bromo, and iodo.

As used herein the term "perfluoro" as in perfluoromethyl or perfluoromethoxy, means that the group in question has fluorine atoms in place of all of the hydrogen atoms.

As used herein "Ac" refers to the group $CH_3C(O)$—.

Certain chemical compounds are referred to herein by their chemical name or by the two-letter code shown below. Compounds CF through CM are included within the scope of Formula I shown above.

BI 4-(3-(2,6-Dimethylbenzyloxy)phenyl)-4-oxobutyric acid
BT 4-[[4-(2,6-Dimethylbenzyloxy)-3-methoxy]phenyl]-4-oxobutyric acid
BU 4-[3-[[N-(4-Trifluoromethylbenzyl)aminocarbonyl]-4-methoxy]phenyl]-4-oxobutyric acid
BV 4-[3-[[N-(2,6-dimethylbenzyl)aminocarbonyl]-4-methoxy]phenyl]-4-oxobutyric acid
CA (2,6-Dimethylbenzyloxy)benzene
CB Methyl 3-(3-(2,6-Dimethylbenzyloxy)phenyl)-3-oxopropionate
CC 3-(3-(2,6,-Dimethylbenzyloxy)phenyl)-4-oxobutyramide
CD 5-(3-(2,6-Dimethylbenzyloxy)phenyl)-5-oxopentanoic acid
CE 4-(3-(2,6-Dimethylbenzyloxy)phenyl)butyric acid
CF 3-(2,6-Dimethylbenzyloxy)phenylacetic acid
CG 3-(2,6-Dimethylbenzyloxy)benzoic acid
CH Ethyl 3-(2,6-dimethylbenzyloxy)benzoate
CI 6-[3-(2,6-Dimethylbenzyloxy)-phenyl]-hexanoic acid
CJ Ethyl 6-[3-(2,6-dimethylbenzyloxy)-phenyl]-hexanoate
CK 5-[3-(2,6-Dimethylbenzyloxy)-phenyl]-pentanoic acid
CL Ethyl 5-[3-(2,6-dimethylbenzyloxy)-phenyl]-pentanoate
CM 3-[3-(2,6-dimethylbenzyloxy)phenyl]-propionic acid
CN Ethyl 3-[3-(2,6-dimethylbenzyloxy)phenyl]-propanoate As used herein the transitional term "comprising" is open-ended. A claim utilizing this term can contain elements in addition to those recited in such claim.

Compounds of the Invention

In an embodiment of the agent, use, method or pharmaceutical composition described above, n is 1; q is 0; t is 0; $R^3$ is hydrogen; and A is phenyl, unsubstituted or substituted by 1 or 2 groups selected from: halo, alkyl having 1 or 2 carbon atoms, perfluoromethyl, alkoxy having 1 or 2 carbon atoms, and perfluoromethoxy. In a more specific embodiment, A is 2,6-dimethylphenyl. Examples of such compounds include 3-(2,6-Dimethylbenzyloxy)phenylacetic acid; 3-(2,6-Dimethylbenzyloxy)benzoic acid; Ethyl 3-(2,6-dimethylbenzyloxy)benzoate; 6-[3-(2,6-Dimethylbenzyloxy)-phenyl]-hexanoic acid; Ethyl 6-[3-(2,6-Dimethylbenzyloxy)-phenyl]-hexanoate; 5-[3-(2,6-Dimethylbenzyloxy)-phenyl]-pentanoic acid; Ethyl 5-[3-(2,6-dimethylbenzyloxy)-phenyl]-pentanoate; 3-[3-(2,6-dimethylbenzyloxy)phenyl]-propionic acid; and Ethyl 3-[3-(2,6-dimethylbenzyloxy)phenyl]-propanoate.

In a preferred embodiment of the biologically active agent of this invention, the agent is in substantially (at least 98%) pure form.

Reaction Schemes

The biologically active agents of the present invention can be made in accordance with the following reaction schemes.

The compound of formula I where m is 0 to 2, q is 0, t is 0 or 1, and n is 1 or 2, $R^3$ is hydrogen, halo, alkoxy having from 1 to 3 carbon atoms or alkyl having from 1 to 3 carbon atoms, and $R^1$ is hydrogen or alkyl having from 1 to 2 carbon atoms, i.e. compounds of formula:

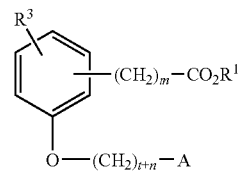

wherein A is described as above, can be prepared via reaction of scheme 1.

In the reaction scheme of Scheme 1, A, t, n, m, and $R^3$ are as above. $R^4$ is alkyl group having 1 to 2 carbon atoms, and Y is a leaving group.

The compound of formula II is converted to the compound of formula V via reaction of step (a) using Mitsunobu condensation of II with III using triphenylphosphine and diethyl azodicarboxylate or diisopropyl azodicarboxylate. The reaction is carried out in a suitable solvent for example tetrahydrofuran. Any of the conditions conventionally used in Mitsunobu reactions can be utilized to carry out the reaction of step (a).

The compound of formula V can also be prepared by etherifying or alkylating the compound of formula II with a compound of formula IV as in reaction of step (a). In the compound of formula IV, Y, include but are not limited to mesyloxy, tosyloxy, chloro, bromo, iodo, and the like. Any conventional method of etherifying of a hydroxyl group by reaction with a leaving group can be utilized to carry out the reaction of step (a).

The compound of formula V is the compound of formula I where $R^1$ is alkyl group having from 1 to 2 carbon atoms. The compound of formula V can be converted to the free acid i.e. the compound of formula I where $R^1$ is H by ester hydrolysis. Any conventional method of ester hydrolysis will produce the compound of formula I where $R^1$ is H.

Reaction Scheme 1

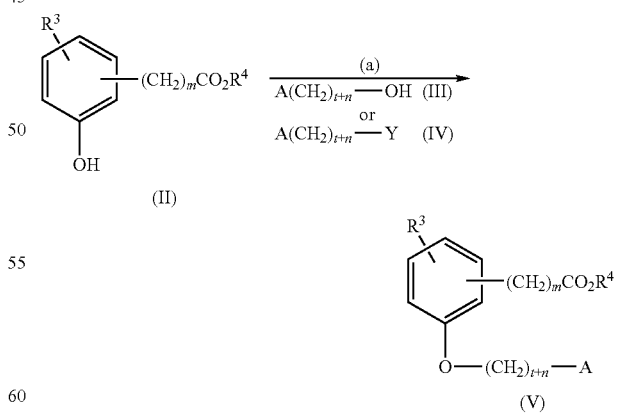

The compound of formula I where m is 3 to 5, q is 0, t is 0 or 1, and n is 1 or 2, $R^3$ is hydrogen, halo, alkoxy having from 1 to 3 carbon atoms or alkyl having from 1 to 3 carbon atoms, and $R^1$ is hydrogen or alkyl having from 1 to 2 carbons, i.e. compounds of formula:

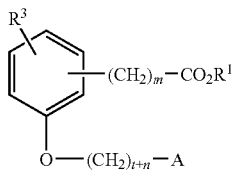

wherein A is described as above, can be prepared via reaction of scheme 2.

In the reaction scheme of Scheme 2, A, t, n, m, $R^1$ and $R^3$ are as above. $R^4$ is alkyl having from 1 to 2 carbon atoms, p is 1 to 3 and Y is a leaving group.

The compound of formula VI is converted to the compound of formula VII via reaction of step (b) using Mitsunobu condensation of VI with III using triphenylphosphine and diethyl azodicarboxylate or diisopropyl azodicarboxylate. The reaction is carried out in a suitable solvent for example tetrahydrofuran. Any of the conditions conventionally used in Mitsunobu reactions can be utilized to carry out the reaction of step (b).

The compound of formula VII can also be prepared by etherifying or alkylating the compound of formula VI with a compound of formula IV via the reaction of step (c) by using suitable base such as potassium carbonate, sodium hydride, triethylamine, pyridine and the like. In the compound of formula IV, Y, include but are not limited to mesyloxy, tosyloxy, chloro, bromo, iodo, and the like. Any conventional conditions to alkylate a hydroxyl group with a halide or leaving group can be utilized to carry out the reaction of step (c). The reaction of step (c) is preferred over step (b) if compound of formula IV is readily available.

The compound of formula VII is converted to the compound of formula IX via reaction of step (d) by alkylating the compound of formula VII with the compound of formula VIII. This reaction is carried out in the presence of approximately a molar equivalent of a conventional base that converts acetophenone to 3-keto ester (i.e. gamma-keto ester). In carrying out this reaction it is generally preferred but not limited to utilize alkali metal salts of hexamethyldisilane such as lithium bis-(trimethylsilyl)amide and the like. Generally this reaction is carried out in inert solvents such as tetrahydrofuran: 1,3-Dimethyl-3,4,5,6-tetrahydro-2 (1H)-pyrimidinone. Generally the reaction is carried out at temperatures of from −65° C. to 25° C. Any of the conditions conventional in such alkylation reactions can be utilized to carry out the reaction of step (d).

The compound of formula IX is converted to the free acid by ester hydrolysis. Any conventional method of ester hydrolysis will produce the compound of formula IX where $R^1$ is H.

The compound of formula IX is converted to the compound of X via reaction of step (e) by reducing the ketone group to $CH_2$ group. The reaction is carried out by heating compound of formula IX with hydrazine hydrate and a base such as KOH or NaOH in suitable solvent such as ethylene glycol. In carrying out this reaction it is generally preferred but not limited to utilize KOH as base. Any of the conditions conventionally used in Wolff-Kishner reduction reactions can be utilized to carry out the reaction of step (e). The compound of formula X is the compound of formula I where $R^1$ is H.

In the compound of formula X, acid can be converted to ester i.e. the compound of formula I where $R^1$ is alkyl having from 1 to 2 carbon atoms by esterification of acid by using catalysts for example $H_2SO_4$, TsOH and the like or by using dehydrating agents for example dicyclohexylcarbodiimide and the like in ethanol or methanol. Any conventional conditions in such esterification reactions can be utilized to produce the compound of formula I where $R^1$ is alkyl having from 1 to 2 carbon atoms.

Reaction Scheme 2

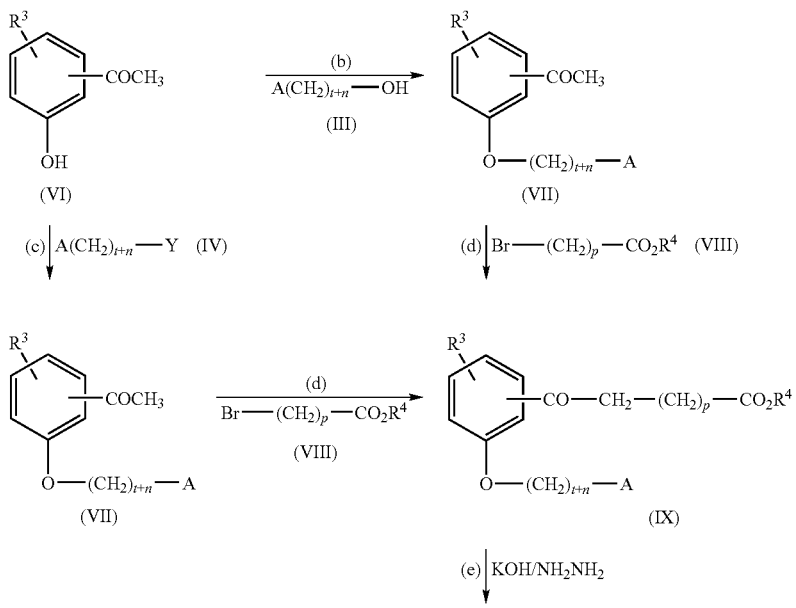

-continued

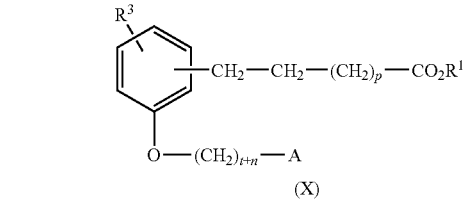

The compound of formula I where q is 1, $R^2$ is an alkyl group having 1 to 3 carbon atoms, m is 3 to 5, t is 0 or 1 and n is 1 or 2, i.e. compounds of the formula:

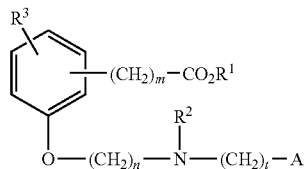

wherein A is described as above, $R^1$ is hydrogen or alkyl having from 1 to 2 carbon atoms, $R^3$ is hydrogen, halo, alkoxy having from 1 to 3 carbon atoms or alkyl having from 1 to 3 carbon atoms, can be prepared via the reaction scheme of Scheme 3.

In the reaction scheme of Scheme 3, t, n, A, $R^1$, $R^3$, and $R^2$ are as above. $R^4$ is alkyl group having from 1 to 2 carbon atoms. Y is chloro or bromo and p is 1 to 3.

The compound of formula XI can be mesylated to furnish the compound of formula XII via reaction of step (f). Any conventional conditions to carry out the mesylation reaction of a hydroxyl group can be utilized to carry out the step (f). The compound of formula XII is then heated with the compound of formula XIII to produce the compound of formula XIV. Any of the conditions conventional to produce amino alcohol can be utilized to carry out the reaction of step (g).

In the compound of formula XIV, alcohol can be displaced by chloro or bromo by treating the compound of formula XIV with thionyl chloride, bromine, and phosphorus tribromide and the like to produce the compound of formula XV. Any conventional method to displace alcohol with chloro or bromo can be utilized to carry out the reaction of step (h).

The compound of formula XV can be reacted with the compound of formula VI via reaction of step (i) in the presence of a suitable base such as potassium carbonate, sodium hydride, triethylamine and the like. The reaction is carried out in conventional solvents such as dimethylformamide, tetrahydrofuran and the like to produce the corresponding compound of formula XVI. Any conventional method of etherification of a hydroxyl group in the presence of base (preferred base being potassium carbonate) with chloro or bromo can be utilized to carry out the reaction of step (i).

The compound of formula XVI can be converted to the compound of formula XVII via reaction of step (j) by alkylating the compound of formula XVI with the compound of formula VIII. This reaction is carried out in the presence of approximately a molar equivalent of a suitable base such as lithium hexamethyldisilane. This reaction is carried out in the same manner as described in connection with the reaction of step (d) of Scheme 2.

The compound of formula XVII can be converted to the free acid by ester hydrolysis. Any conventional method of ester hydrolysis will produce the compound of formula XVII where $R^1$ is H.

The compound of formula XVII can be converted to the compound of XVIII via reaction of step (k) by reducing the ketone group to $CH_2$ group. The reaction can be carried out by heating compound of formula XVII with hydrazine hydrate and base such as KOH or NaOH in suitable solvent such as ethylene glycol. In carrying out this reaction it is generally preferred but not limited to utilize KOH as base. Any of the conditions conventionally used in Wolff-Kishner reduction reactions can be utilized to carry out the reaction of step (k). The compound of formula XVIII is the compound of formula I where $R^1$ is H.

In the compound of formula XVIII, acid can be converted to ester i.e. the compound of formula I where $R^1$ is alkyl having from 1 to 2 carbon atoms by esterification of acid by using catalysts for example $H_2SO_4$, TsOH and the like or by using dehydrating agents for example dicyclohexylcarbodiimide and the like in ethanol or methanol. Any conventional conditions in such esterification reactions can be utilized to produce the compound of formula I where $R^1$ is alkyl having from 1 to 2 carbon atoms.

Reaction Scheme 3

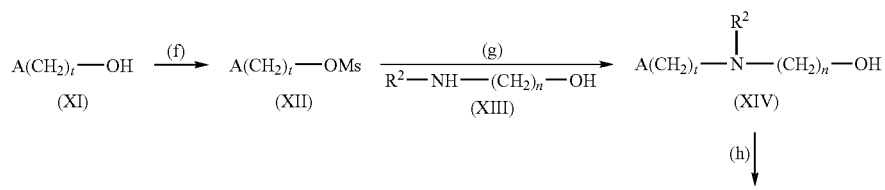

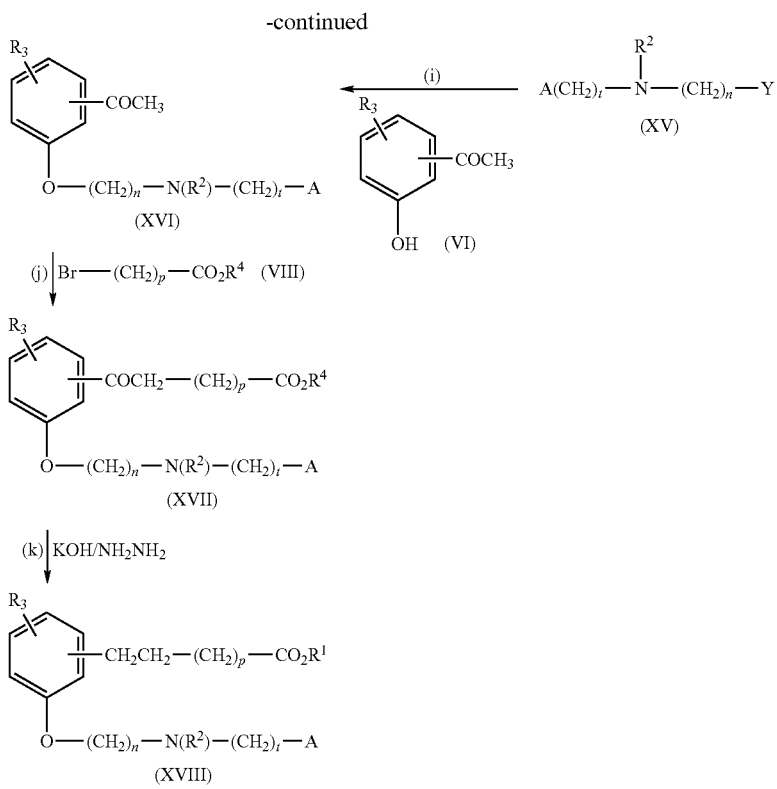

The compound of formula I where m is 0 to 2, q is 1, t is 0 or 1, and n is 1 or 2, $R^3$ is hydrogen, halo, alkoxy having from 1 to 3 carbon atoms or alkyl having from 1 to 3 carbon atoms, and $R^1$ is hydrogen or alkyl having from 1 to 2 carbons, i.e. compounds of formula:

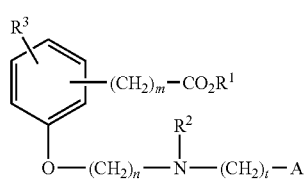

wherein A is described as above, can be prepared via reaction of Scheme 4.

In the reaction of Scheme 4, t, n, A, $R^3$, and $R^2$ are as above. $R^4$ is alkyl group having from 1 to 2 carbon atoms. Y is chloro or bromo.

The compound of formula XV (prepared in the same manner as described in the reaction of scheme 3) can be reacted with a compound of formula II via reaction of step (l) in the presence of a suitable base such as potassium carbonate, sodium hydride, triethylamine and the like. The reaction can be carried out in conventional solvents such as dimethylformamide, tetrahydrofuran, dichloromethane and the like to produce the corresponding compound of formula XIX. Any conventional conditions of etherification of a hydroxyl group in the presence of base (preferred base being potassium carbonate) with chloro or bromo can be utilized to carry out the reaction of step (l).

The compound of formula XIX is the compound of formula I where $R^1$ is alkyl group having from 1 to 2 carbon atoms. The compound of formula XIX can be converted to the free acid i.e. the compound of formula I where $R^1$ is H by ester hydrolysis. Any conventional method of ester hydrolysis will produce the compound of formula I where $R^1$ is H.

Reaction Scheme 4

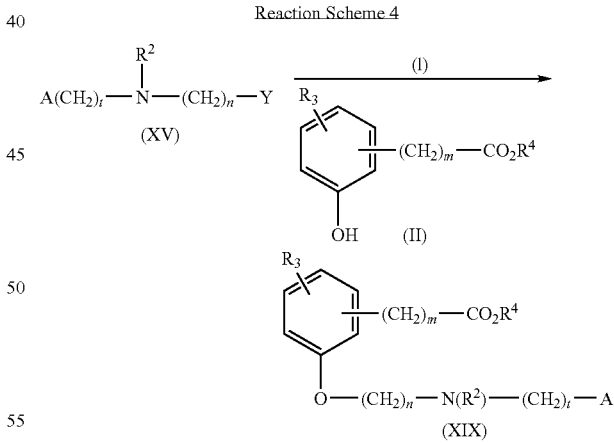

The compound of formula III, where t is 0 or 1, n is 1 or 2, i.e. compounds of formula:

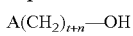

wherein A is described as above, can be prepared via reaction of scheme 5.

In the reaction of Scheme 5, A is described as above and Y is a leaving group.

The compound of formula XX can be reduced to the compound of formula XXI via reaction of step (m). The reaction is carried out utilizing a conventional reducing agent for example alkali metal hydride such as lithium aluminum hydride. The reaction is carried out in a suitable solvent, such as tetrahydrofuran. Any of the conditions conventional in such reduction reactions can be utilized to carry out the reaction of step (m).

The compound of formula XXI is the compound of formula III where t is 0 and n is 1.

The compound of formula XXI can be converted to the compound of formula XXII by displacing hydroxyl group with a halogen group preferred halogen being bromo or chloro. Appropriate halogenating reagents include but are not limited to thionyl chloride, bromine, phosphorous tribromide, carbon tetrabromide and the like. Any conditions conventional in such halogenation reactions can be utilized to carry out the reaction of step (n).

The compound of formula XXII is the compound of formula IV where t is 0 and n is 1.

The compound of formula XXII can be converted to the compound of formula XXIII by reacting XXII with an alkali metal cyanide for example sodium or potassium cyanide. The reaction is carried out in a suitable solvent, such as dimethyl sulfoxide. Any of the conditions conventionally used in the preparation of nitrile can be utilized to carry out the reaction of step (o).

The compound of formula XXV can be converted to the compound of formula XXVI via reaction of step (r) in the same manner as described hereinbefore in connection with the reaction of step (n).

The compound of formula XXVI is the compound of formula IV where t is 1 and n is 1.

The compound of formula XXVI can be reacted with diethyl malonate utilizing a suitable base for example sodium hydride to give compound of formula XXVII. The reaction is carried out in suitable solvents, such as dimethylformamide, tetrahydrofuran and the like. Any of the conditions conventional in such alkylation reactions can be utilized to carry out the reaction of step (s).

The compound of formula XXVII can be hydrolyzed by acid or base to give compound of formula XXVIII via reaction of step (t).

The compound of formula XXVIII can be converted to the compound of formula XXIX via reaction of step (u) in the same manner as described hereinbefore in connection with the reaction of step (m).

The compound of formula XXIX is the compound of formula III where t is 1 and n is 2.

The compound of formula XXIX can be converted to the compound of formula XXX via reaction of step (v) in the same manner as described hereinbefore in connection with the reaction of step (n). The compound of formula XXX is the compound of formula IV where t is 1 and n is 2.

Reaction Scheme 5

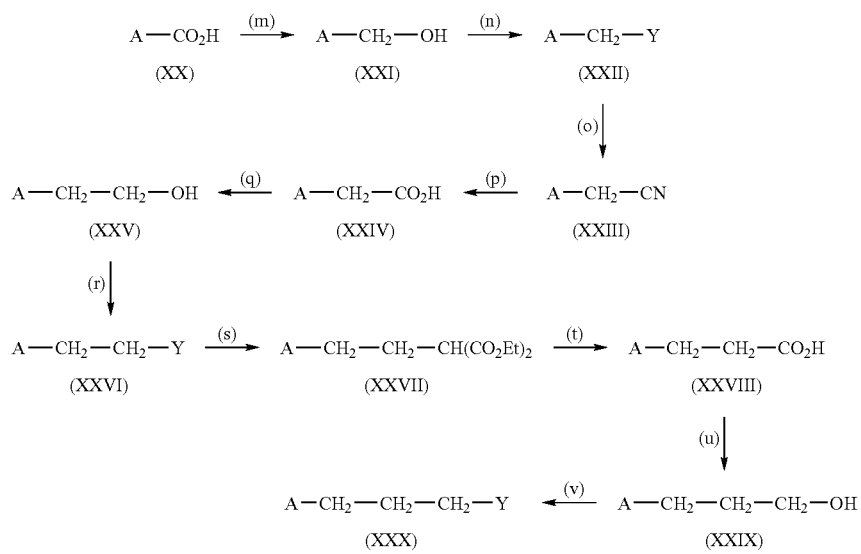

The compound of formula XXIII can be converted to the compound of formula XXIV via reaction step (p) by acid or base hydrolysis. In carrying out this reaction it is generally preferred to utilize basic hydrolysis, for example aqueous sodium hydroxide. Any of the conditions conventionally used in hydrolysis of nitrile can be utilized to carry out the reaction of step (p).

The compound of formula XXIV can be reduced to give the compound of formula XXV via reaction of step (q). This reaction can be carried out in the same manner as described hereinbefore in the reaction of step (m).

The compound of formula XXV is the compound of formula III where t is 1 and n is 1.

The compound of formula II, where m is 0, $R^4$ is alkyl group having from 1 to 2 carbon atoms and $R^3$ is halo, alkoxy having from 1 to 3 carbon atoms or alkyl having from 1 to 3 carbon atoms, i.e. compounds of formula:

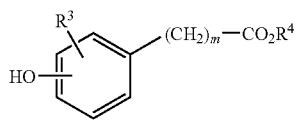

can be prepared via reaction of scheme 6.

In the reaction of Scheme 6, $R^1$ is H. $R^3$ and $R^4$ are as above.

In the compound of formula XXXI, $R^1$ is H. The compound of formula XXXI can be converted to the compound of formula II via reaction of step (w) by esterification of compound of formula XXXI with methanol or ethanol. The reaction can be carried out either by using catalysts for example $H_2SO_4$, TsOH and the like or by using dehydrating agents for example dicyclohexylcarbodiimide and the like. Any of the conditions conventional in such esterification reactions can be utilized to carry out the reaction of step (w).

Reaction Scheme 6

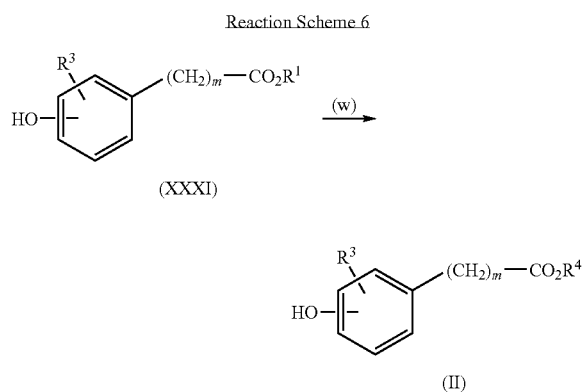

The compound of formula VI where $R^3$ is halo, alkoxy having from 1 to 3 carbon atoms or alkyl having from 1 to 3 carbon atoms, i.e. compounds of formula:

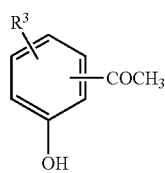

can be prepared via reaction of scheme 7.

In the reaction of Scheme 7, m is 0 and $R^1$ is H and $R^3$ is halo, alkoxy having from 1 to 3 carbon atoms or alkyl having from 1 to 3 carbon atoms.

In Reaction Scheme 7 m is 0. Reaction Scheme 7 is analogous to the method of George M Rubottom et al., J. Org. Chem. 1983, 48, 1550-1552.

Reaction Scheme 7

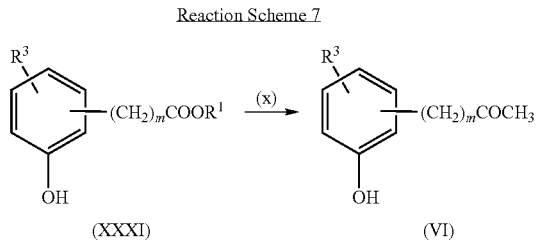

The compound of formula II where m is 1 to 2, $R^4$ is alkyl group having from 1 to 2 carbon atoms and $R^3$ is halo, alkoxy having from 1 to 3 carbon atoms or alkyl having from 1 to 3 carbon atoms, i.e. compounds of formula:

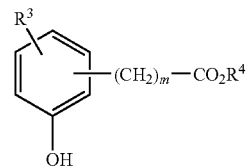

can be prepared via reaction of scheme 8.

In the reaction of Scheme 8, $R^1$ is H, $R^3$ is halo, alkoxy having from 1 to 3 carbon atoms or alkyl having from 1 to 3 carbon atoms, $R^4$ is alkyl group having 1 to 2 carbon atoms and $R^5$ is a hydroxy protecting group.

The compound of formula II where m is 0 can be converted to the compound of formula XXXII via reaction of step (y) first by protecting the hydroxy group by utilizing suitable protecting groups such as those described in Protecting Groups in Organic Synthesis by T. Greene and then by deprotecting the ester group by ester hydrolysis. Any conventional method of ester hydrolysis will produce the compound of formula XXXII where $R^1$ is H.

The compound of formula XXXII can be reduced to the compound of formula XXXIII by utilizing conventional reducing reagent that converts acid to an alcohol via reaction of step (z). In carrying out this reaction it is generally preferred but not limited to utilize lithium aluminum hydride. The reaction is carried out in a suitable solvent such as tetrahydrofuran and the like. Any of the conditions conventional in such reduction reactions can be utilized to carry out the reaction of step (z).

The compound of formula XXXIII can be converted to the compound of formula XXXIV by displacing hydroxy group with a halogen preferred halogen being bromo or chloro. Appropriate halogenating reagents include but are not limited to thionyl chloride, bromine, phosphorous tribromide, carbon tetrabromide and the like. Any conditions conventional in such halogenation reactions can be utilized to carry out the reaction of step (a').

The compound of formula XXXIV can be converted to the compound of formula XXXV by reacting XXXIV with an alkali metal cyanide for example sodium or potassium cyanide. The reaction is carried out in a suitable solvent such as dimethyl sulfoxide. Any of the conditions conventionally used in the preparation of nitrites can be utilized to carry out the reaction of step (b').

The compound of formula XXXV can be converted to the compound of formula XXXVI via reaction step (c') by acid or base hydrolysis. In carrying out this reaction, it is generally preferred to utilize basic hydrolysis, for example aqueous sodium hydroxide. Any of the conditions conventional for the hydrolysis of nitrile can be utilized to carry out the reaction of step (c').

The compound of formula XXXVI can be converted to the compound of formula XXXVII via reaction of step (d') by removal of hydroxy protecting group utilizing suitable deprotecting reagents such as those described in Protecting Groups in Organic Synthesis by T. Greene.

The compound of formula XXXVII can be converted to compound of formula II where m is 1 and $R^4$ is alkyl group having from 1 or 2 carbon atoms by esterification of compound of formula XXXVII with methanol or ethanol. The reaction can be carried out either by using catalysts for example $H_2SO_4$, TsOH and the like or by using dehydrating agents for example dicyclohexylcarbodiimide and the like.

Any of the conditions conventional in such esterification reactions can be utilized to carry out the reaction.

The compound of formula XXXIV can be reacted with diethyl malonate utilizing a suitable base for example sodium hydride to give compound of formula XXXVIII. The reaction is carried out in suitable solvents, such as dimethylformamide, tetrahydrofuran and the like. Any of the conditions conventional in such alkylation reactions can be utilized to carry out the reaction of step (e').

The compound of formula XXXVIII can be hydrolyzed by acid or base and removal of hydroxy protecting group utilizing suitable deprotecting reagents such as those described in Protecting Groups in Organic Synthesis by T. Greene to give compound of formula XXXIX via reaction of step (f').

The compound of formula XXXIX can be converted to the compound of formula II where m is 2 and $R^4$ is alkyl group having from 1 or 2 carbon atoms by esterification of compound of formula XXXIX with methanol or ethanol. The reaction can be carried out either by using catalysts for example $H_2SO_4$, TsOH and the like or by using dehydrating agents for example dicyclohexylcarbodiimide and the like. Any of the conditions conventional in such esterification reactions can be utilized to carry out the reaction.

The compound of formula XXXI, where m is 0, $R^1$ is H and $R^3$ is halo, i.e. compounds of formula:

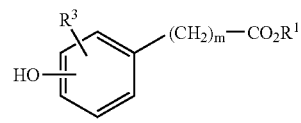

are either commercially available or can be prepared according to the methods described in the literature as follows:

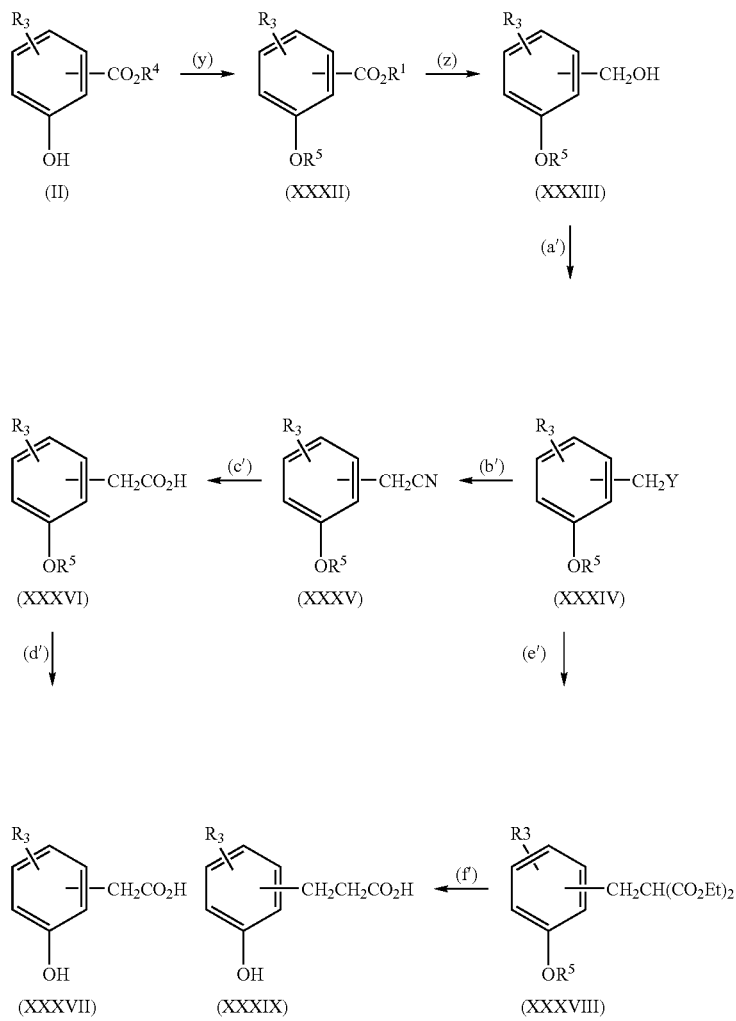

1. 3-Br or F-2-OHC$_6$H$_3$CO$_2$H

Canadian Journal of Chemistry (2001), 79(11) 1541-1545.

2. 4-Br-2-OHC$_6$H$_3$CO$_2$H

WO 9916747 or JP 04154773.

3. 2-Br-6-OHC$_6$H$_3$CO$_2$H

JP 47039101.

4. 2-Br-3-OHC$_6$H$_3$CO$_2$H

WO 9628423.

5. 4-Br-3-OHC$_6$H$_3$CO$_2$H

WO 2001002388.

6. 3-Br-5-OHC$_6$H$_3$CO$_2$H

Journal of labelled Compounds and Radiopharmaceuticals (1992), 31 (3), 175-82.

7. 2-Br-5-OHC$_6$H$_3$CO$_2$H and 3-Cl-4-OHC$_6$H$_3$CO$_2$H

WO 9405153 and U.S. Pat. No. 5,519,133.

8. 2-Br-4-OHC$_6$H$_3$CO$_2$H and 3-Br-4-OHC$_6$H$_3$CO$_2$H

WO 20022018323

9. 2-Cl-6-OHC$_6$H$_3$CO$_2$H

JP 06293700

10. 2-Cl-3-OHC$_6$H$_3$CO$_2$H

Proceedings of the Indiana Academy of Science (1983), Volume date 1982, 92, 145-51.

11. 3-Cl-5-OHC$_6$H$_3$CO$_2$H

WO 2002000633 and WO 2002044145.

12. 2-Cl-5-OHC$_6$H$_3$CO$_2$H

WO 9745400.

13. 5-I-2-OHC$_6$H$_3$CO$_2$H and 3-I, 2-OHC$_6$H$_3$CO$_2$H

Z. Chem. (1976), 16(8), 319-320.

14. 4-I-2-OHC$_6$H$_3$CO$_2$H

Journal of Chemical Research, Synopses (1994), (11), 405.

15. 6-I-2-OHC$_6$H$_3$CO$_2$H

U.S. Pat. No. 4,932,999.

16. 2-I-3-OHC$_6$H$_3$CO$_2$H and 4-I-3-OHC$_6$H$_3$CO$_2$H

WO 9912928.

17. 5-I-3-OHC$_6$H$_3$CO$_2$H

J. Med. Chem. (1973), 16(6), 684-7.

18. 2-I-4-OHC$_6$H$_3$CO$_2$H

Collection of Czechoslovak Chemical Communications, (1991), 56(2), 459-77.

19. 3-I-4-OHC$_6$H$_3$CO$_2$,

J.O.C. (1990), 55(18), 5287-91.

The compound of formula XXXI, where m is 0, R$^1$ is H and R$^3$ is alkoxy having from 1 to 3 carbon atoms, and the phenyl ring is substituted as shown below:

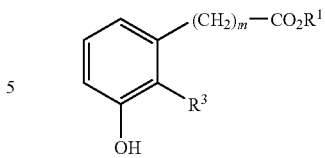

can be synthesized via the reaction of scheme 9.

In the reaction of Scheme 9, R$^1$ and R$^3$ are as above, and R$^4$ is alkyl group having from 1 to 2 carbon atoms.

The compound of formula XL can be converted to the compound of formula XLI by reducing aldehyde to primary alcohol. In carrying out this reaction, it is preferred but not limited to use sodium borohydride as the reducing reagent. Any of the conditions suitable in such reduction reactions can be utilized to carry out the reaction of step (g').

The compound of formula XLI can be converted to the compound of formula XLII via reaction of step (h') by protecting 1-3 Diols by using 1,1,3,3-Tetraisopropyldisiloxane. The suitable conditions for this protecting group can be described in the Protecting Groups in Organic Synthesis by T. Greene.

The compound of formula XLII can be converted to the compound of formula XLIII via reaction of step (i') by protecting phenol group by using benzyl bromide. The suitable conditions for this protecting group can be described in the Protecting Groups in Organic Synthesis by T. Greene.

The compound of formula XLIII can be converted to the compound of formula XLIV by deprotection using tetrabutylammonium fluoride via reaction of step (j'). The suitable conditions for the deprotection can be described in the Protecting Groups in Organic Synthesis by T. Greene.

The compound of formula XLIV can be converted to compound of formula XLV via reaction of step (k') by oxidation. Any conventional oxidizing group that converts primary alcohol to an acid for example chromium oxide and the like can be utilized to carry out the reaction of step (k').

The compound of formula XLV can be converted to the compound of formula XLVI by esterification of compound of formula XLV with methanol or ethanol. The reaction can be carried out either by using catalysts for example H$_2$SO$_4$, TsOH and the like or by using dehydrating agents for example dicyclohexylcarbodiimide and the like. Any of the conditions conventional in such esterification reactions can be utilized to carry out the reaction of step (l').

The compound of formula XLVI can be converted to the compound of formula XLVII by etherifying or alkylating the compound of formula XLVI with methyl halide or ethyl halide or propyl halide by using suitable base for example potassium carbonate, sodium hydride and the like. The reaction is carried out in conventional solvents, such as terahydrofuran, dimethylformamide. The reaction is generally carried out at temperatures of from 0° C. to 40° C. Any of the conditions suitable in such alkylation reactions can be utilized to carry out the reaction of step (m').

The compound of formula XLVII can be converted to the compound of formula XLVIII by deprotection of ester and benzyl groups. The suitable deprotecting conditions can be described in the Protecting Groups in Organic Synthesis by T. Greene.

Reaction Scheme 9

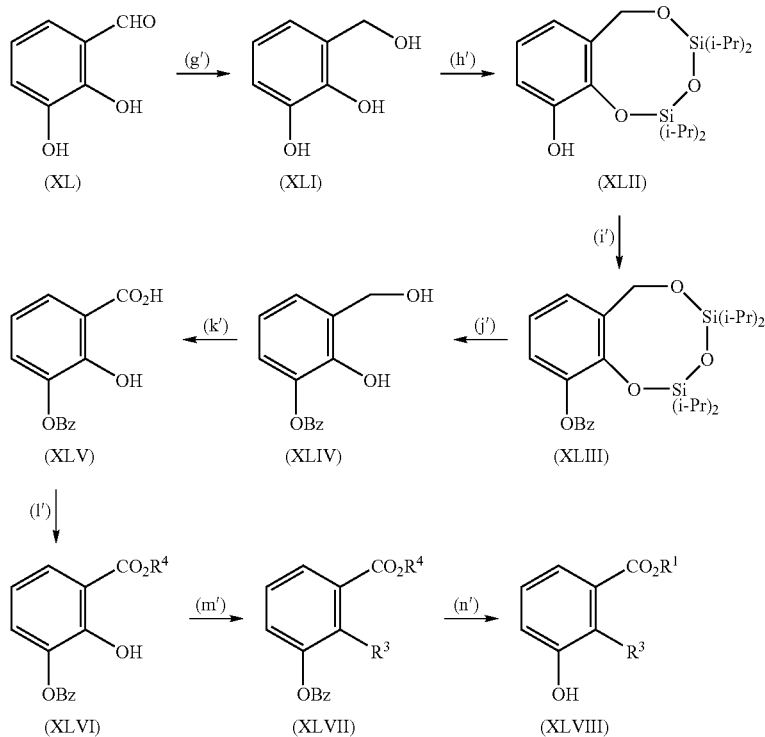

Other compounds of formula XXXI where m is 0, $R^1$ is H and $R^3$ is alkoxy having from 1 to 3 carbon atoms, i.e. compounds of formula:

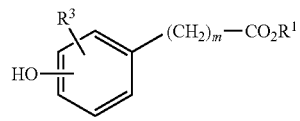

are either commercially available or can be prepared according to the methods described in the literature as follows:

1. $2\text{-OMe-4-OHC}_6\text{H}_3\text{CO}_2\text{H}$

US 2001034343 or WO 9725992.

2. $5\text{-OMe-3-OHC}_6\text{H}_3\text{CO}_2\text{H}$

J.O.C (2001), 66(23), 7883-88.

3. $2\text{-OMe-5-OHC}_6\text{H}_3\text{CO}_2\text{H}$

U.S. Pat. No. 6,194,406 (Page 96) and Journal of the American Chemical Society (1985), 107(8), 2571-3.

4. $3\text{-OEt-5-OHC}_6\text{H}_3\text{CO}_2\text{H}$

Taiwan Kexue (1996), 49(1), 51-56.

5. $4\text{-OEt-3-OHC}_6\text{H}_3\text{CO}_2\text{H}$

WO 9626176

6. $2\text{-OEt-4-OHC}_6\text{H}_3\text{CO}_2\text{H}$

Takeda Kenkyusho Nempo (1965), 24,221-8.

JP 07070025.

7. $3\text{-OEt-4-OHC}_6\text{H}_3\text{CO}_2\text{H}$

WO 9626176.

8. $3\text{-OPr-2-OHC}_6\text{H}_3\text{CO}_2\text{H}$

JP 07206658, DE 2749518.

9. $4\text{-OPr-2-OHC}_6\text{H}_3\text{CO}_2\text{H}$

Farmacia (Bucharest) (1970), 18(8), 461-6.

JP 08119959.

10. $2\text{-OPr-5-OHC}_6\text{H}_3\text{CO}_2\text{H}$ and $2\text{-OEt-5-OHC}_6\text{H}_3\text{CO}_2\text{H}$ Adapt synthesis from U.S. Pat. No. 6,194,406 (Page 96) by using propyl iodide and ethyl iodide.

11. $4\text{-OPr-3-OHC}_6\text{H}_3\text{CO}_2\text{H}$

Adapt synthesis from WO 9626176

12. $2\text{-OPr-4-OHC}_6\text{H}_3\text{CO}_2\text{H}$

Adapt synthesis from Takeda Kenkyusho Nempo (1965), 24,221-8 by using propyl halide.

13. $4\text{-OEt-3-OHC}_6\text{H}_3\text{CO}_2\text{H}$

Biomedical Mass Spectrometry (1985), 12(4), 163-9.

14. $3\text{-OPr-5-OHC}_6\text{H}_3\text{CO}_2\text{H}$

Adapt synthesis from Taiwan Kexue (1996), 49(1), 51-56 by using propyl halide.

The compound of formula XXXI, where m is 0, $R^1$ is H and $R^3$ is an alkyl having 1 to 3 carbon atoms, i.e. compounds of formula:

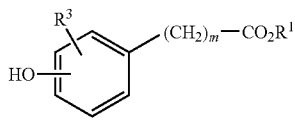

are either commercially available or can be prepared according to the methods described in the literature as follows:

1. 5-Me-3-OHC$_6$H$_3$CO$_2$H and 2-Me-5-OHC$_6$H$_3$CO$_2$H

WO 9619437.

J.O.C. 2001, 66, 7883-88.

2. 2-Me-4-OHC$_6$H$_3$CO$_2$H

WO 8503701.

3. 3-Et-2-OHC$_6$H$_3$CO$_2$H and 5-Et-2-OHC$_6$H$_3$CO$_2$H

J. Med. Chem. (1971), 14(3), 265.

4. 4-Et-2-OHC$_6$H$_3$CO$_2$H

Yaoxue Xuebao (1998), 33(1), 67-71.

5. 2-Et-6-OHC$_6$H$_3$CO$_2$H and 2-n-Pr-6-OHC$_6$H$_3$CO$_2$H

J. Chem. Soc., Perkin Trans 1 (1979), (8), 2069-78.

6. 2-Et-3-OHC$_6$H$_3$CO$_2$H

JP 10087489 and WO 9628423.

7. 4-Et-3-OHC$_6$H$_3$CO$_2$H

J.O.C. 2001, 66, 7883-88.

WO 9504046.

8. 2-Et-5-OHC$_6$H$_3$CO$_2$H

J.A.C.S (1974), 96(7), 2121-9.

b 9. 2-Et-4-OHC$_6$H$_3$CO$_2$H and 3-Et-4-OHC$_6$H$_3$CO$_2$H

JP 04282345.

10. 3-n-Pr-2-OHC$_6$H$_3$CO$_2$H

J.O.C (1991), 56(14), 4525-29.

11. 4-n-Pr-2-OHC$_6$H$_3$CO$_2$H

EP 279630.

12. 5-n-Pr-2-OHC$_6$H$_3$CO$_2$H

J. Med. Chem. (1981), 24(10), 1245-49.

13. 2-n-Pr-3-OHC$_6$H$_3$CO$_2$H

WO 9509843 and WO 9628423.

14. 4-n-Pr-3-OHC$_6$H$_3$CO$_2$H

WO 9504046.

15. 2-n-Pr-5-OHC$_6$H$_3$CO$_2$H

Synthesis can be adapted from J.A.C.S (1974), 96(7), 2121-9 by using ethyl alpha formylvalerate.

16. 3-n-Pr-4-OHC$_6$H$_3$CO$_2$H

Polymer (1991), 32(11) 2096-105.

17. 2-n-Pr-4-OHC$_6$H$_3$CO$_2$H

3-Propylphenol can be methylated to 3-Propylanisole, which was then formylated to 4-Methoxy-3-benzaldehyde. The aldehyde can be oxidized by Jone's reagent to give corresponding acid and deprotection of methyl group by BBr$_3$ will give the title compound.

18. 1. 3-Et-5-OHC$_6$H$_3$CO$_2$H and 3-Pr-n-5-OHC$_6$H$_3$CO$_2$H

Adapt synthesis from J.O.C. 2001, 66, 7883-88 by using 2-Ethylacrolein and 2-Propylacrolein.

Use in Methods of Treatment

This invention provides a method for treating a mammalian subject with a condition selected from the group consisting of insulin resistance syndrome and diabetes (both primary essential diabetes such as Type I Diabetes or Type II Diabetes and secondary nonessential diabetes), comprising administering to the subject an amount of a biologically active agent as described herein effective to treat the condition. In accordance with the method of this invention a symptom of diabetes or the chance of developing a symptom of diabetes, such as atherosclerosis, obesity, hypertension, hyperlipidemia, fatty liver disease, nephropathy, neuropathy, retinopathy, foot ulceration and cataracts, each such symptom being associated with diabetes, can be reduced. This invention also provides a method for treating hyperlipidemia comprising administering to the subject an amount of a biologically active agent as described herein effective to treat the condition. As shown in the Examples, compounds reduce serum triglycerides and free fatty acids in hyperlipidemic animals. This invention also provides a method for treating cachexia comprising administering to the subject an amount of a biologically active agent as described herein effective to treat the cachexia. This invention also provides a method for treating obesity comprising administering to the subject an amount of a biologically active agent as described herein effective to treat the condition. This invention also provides a method for treating a condition selected from atherosclerosis or arteriosclerosis comprising administering to the subject an amount of a biologically active agent as described herein effective to treat the condition. The active agents of this invention are effective to treat hyperlipidemia, fatty liver disease, cachexia, obesity, atherosclerosis or arteriosclerosis whether or not the subject has diabetes or insulin resistance syndrome. The agent can be administered by any conventional route of systemic administration. Preferably the agent is administered orally. Accordingly, it is preferred for the medicament to be formulated for oral administration. Other routes of administration that can be used in accordance with this invention include rectally, parenterally, by injection (e.g. intravenous, subcutaneous, intramuscular or intraperitioneal injection), or nasally.

Further embodiments of each of the uses and methods of treatment of this invention comprise administering any one of the embodiments of the biologically active agents described above. In the interest of avoiding unnecessary redundancy, each such agent and group of agents is not being repeated, but they are incorporated into this description of uses and methods of treatment as if they were repeated.

Many of the diseases or disorders that are addressed by the compounds of the invention fall into two broad categories: Insulin resistance syndromes and consequences of chronic hyperglycemia. Dysregulation of fuel metabolism, especially insulin resistance, which can occur in the absence of diabetes (persistent hyperglycemia) per se, is associated with a variety of symptoms, including hyperlipidemia, atherosclerosis, obesity, essential hypertension, fatty liver disease (NASH; nonalcoholic steatohepatitis), and, especially in the context of cancer or systemic inflammatory disease, cachexia. Cachexia can also occur in the context of Type I Diabetes or late-stage Type II Diabetes. By improving tissue fuel metabolism, active agents of the invention are useful for preventing or ameliorating diseases and symptoms associated with insulin resistance, as is demonstrated in animals in the Examples. While a cluster of signs and symptoms associated with insulin resistance may coexist in an individual patient, it many cases only one symptom may dominate, due to individual differences in vulnerability of the many physiological systems affected by insulin resistance. Nonetheless, since insulin resistance is a major contributor to many disease conditions, drugs which address this cellular and molecular defect are useful for prevention or amelioration of virtually any symptom in any organ system that may be due to, or exacerbated by, insulin resistance.

When insulin resistance and concurrent inadequate insulin production by pancreatic islets are sufficiently severe, chronic hyperglycemia occurs, defining the onset of Type II diabetes mellitus (NIDDM). In addition to the metabolic disorders related to insulin resistance indicated above, disease symptoms secondary to hyperglycemia also occur in patients with NIDDM. These include nephropathy, peripheral neuropathy, retinopathy, microvascular disease, ulceration of the extremities, and consequences of nonenzymatic glycosylation of proteins, e.g. damage to collagen and other connective tissues. Attenuation of hyperglycemia reduces the rate of onset and severity of these consequences of diabetes. Because, as is demonstrated in the Examples, active agents and compositions of the invention help to reduce hyperglycemia in diabetes, they are useful for prevention and amelioration of complications of chronic hyperglycemia.

Both human and non-human mammalian subjects can be treated in accordance with the treatment method of this invention. The optimal dose of a particular active agent of the invention for a particular subject can be determined in the clinical setting by a skilled clinician. In the case of oral administration to a human for treatment of disorders related to insulin resistance, diabetes, hyperlipidemia, fatty liver disease, cachexia or obesity the agent is generally administered in a daily dose of from 1 mg to 400 mg, administered once or twice per day. In the case of oral administration to a mouse the agent is generally administered in a daily dose from 1 to 300 mg of the agent per kilogram of body weight. Active agents of the invention are used as monotherapy in diabetes or insulin resistance syndrome, or in combination with one or more other drugs with utility in these types of diseases, e.g. insulin releasing agents, prandial insulin releasers, biguanides, or insulin itself. Such additional drugs are administered in accord with standard clinical practice. In some cases, agents of the invention will improve the efficacy of other classes of drugs, permitting lower (and therefore less toxic) doses of such agents to be administered to patients with satisfactory therapeutic results. Established safe and effective dose ranges in humans for representative compounds are: metformin 500 to 2550 mg/day; glyburide 1.25 to 20 mg/day; GLUCOVANCE (combined formulation of metformin and glyburide) 1.25 to 20 mg/day glyburide and 250 to 2000 mg/day metformin; atorvastatin 10 to 80 mg/day; lovastatin 10 to 80 mg/day; pravastatin 10 to 40 mg/day; and simvastatin 5-80 mg/day; clofibrate 2000 mg/day; gemfibrozil 1200 to 2400 mg/day, rosiglitazone 4 to 8 mg/day; pioglitazone 15 to 45 mg/day; acarbose 75-300 mg/day; repaglinide 0.5 to 16 mg/day.

Type I Diabetes Mellitus: A patient with Type I diabetes manages their disease primarily by self-administration of one to several doses of insulin per day, with frequent monitoring blood glucose to permit appropriate adjustment of the dose and timing of insulin administration. Chronic hyperglycemia leads to complications such as nephropathy, neuropathy, retinopathy, foot ulceration, and early mortality; hypoglycemia due to excessive insulin dosing can cause cognitive dysfunction or unconsciousness. A patient with Type I diabetes is treated with 1 to 400 mg/day of an active agent of this invention, in tablet or capsule form either as a single or a divided dose. The anticipated effect will be a reduction in the dose or frequency of administration of insulin required to maintain blood glucose in a satisfactory range, and a reduced incidence and severity of hypoglycemic episodes. Clinical outcome is monitored by measurement of blood glucose and glycosylated hemoglobin (an index of adequacy of glycemic control integrated over a period of several months), as well as by reduced incidence and severity of typical complications of diabetes. A biologically active agent of this invention can be administered in conjunction with islet transplantation to help maintain the anti-diabetic efficacy of the islet transplant.

Type II Diabetes Mellitus: A typical patient with Type II diabetes (NIDDM) manages their disease by programs of diet and exercise as well as by taking medications such as metformin, glyburide, repaglinide, rosiglitazone, or acarbose, all of which provide some improvement in glycemic control in some patients, but none of which are free of side effects or eventual treatment failure due to disease progression. Islet failure occurs over time in patients with NIDDM, necessitating insulin injections in a large fraction of patients. It is anticipated that daily treatment with an active agent of the invention (with or without additional classes of antidiabetic medication) will improve glycemic control, reduce the rate of islet failure, and reduce the incidence and severity of typical symptoms of diabetes. In addition, active agents of the invention will reduce elevated serum triglycerides and fatty acids, thereby reducing the risk of cardiovascular disease, a major cause of death of diabetic patients. As is the case for all other therapeutic agents for diabetes, dose optimization is done in individual patients according to need, clinical effect, and susceptibility to side effects.

Hyperlipidemia: Elevated triglyceride and free fatty acid levels in blood affect a substantial fraction of the population and are an important risk factor for atherosclerosis and myocardial infarction. Active agents of the invention are useful for reducing circulating triglycerides and free fatty acids in hyperlipidemic patients. Hyperlipidemic patients often also have elevated blood cholesterol levels, which also increase the risk of cardiovascular disease. Cholesterol-lowering drugs such as HMG-CoA reductase inhibitors ("statins") can be administered to hyperlipidemic patients in addition to agents of the invention, optionally incorporated into the same pharmaceutical composition.

Fatty Liver Disease: A substantial fraction of the population is affected by fatty liver disease, also known as nonalcoholic steatohepatitis (NASH); NASH is often associated with obesity and diabetes. Hepatic steatosis, the presence of droplets of triglycerides with hepatocytes, predisposes the liver to chronic inflammation (detected in biopsy samples as infiltration of inflammatory leukocytes), which can lead to fibrosis and cirrhosis. Fatty liver disease is generally detected by observation of elevated serum levels of liver-specific enzymes such as the transaminases ALT and AST, which serve as indices of hepatocyte injury, as well as by presentation of symptoms which include fatigue and pain in the region of the liver, though definitive diagnosis often requires a biopsy. The anticipated benefit is a reduction in liver inflammation and fat content, resulting in attenuation, halting, or reversal of the progression of NASH toward fibrosis and cirrhosis.

Pharmaceutical Compositions

This invention provides a pharmaceutical composition comprising a biologically active agent as described herein and a pharmaceutically acceptable carrier. Further embodiments of the pharmaceutical composition of this invention comprise any one of the embodiments of the biologically active agents described above. In the interest of avoiding unnecessary redundancy, each such agent and group of agents is not being repeated, but they are incorporated into this description of pharmaceutical compositions as if they were repeated.

Preferably the composition is adapted for oral administration, e.g. in the form of a tablet, coated tablet, dragee, hard or soft gelatin capsule, solution, emulsion or suspension. In general the oral composition will comprise from 1 mg to 400 mg of such agent. It is convenient for the subject to swallow one or two tablets, coated tablets, dragees, or gelatin capsules per day. However the composition can also be adapted for administration by any other conventional means of systemic administration including rectally, e.g. in the form of suppositories, parenterally, e.g. in the form of injection solutions, or nasally.

The biologically active compounds can be processed with pharmaceutically inert, inorganic or organic carriers for the production of pharmaceutical compositions. Lactose, corn starch or derivatives thereof, talc, stearic acid or its salts and the like can be used, for example, as such carriers for tablets, coated tablets, dragees and hard gelatin capsules. Suitable carriers for soft gelatin capsules are, for example, vegetable oils, waxes, fats, semi-solid and liquid polyols and the like. Depending on the nature of the active ingredient no carriers are, however, usually required in the case of soft gelatin capsules, other than the soft gelatin itself. Suitable carriers for the production of solutions and syrups are, for example, water, polyols, glycerol, vegetable oils and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, coating agents or antioxidants. They can also contain still other therapeutically valuable substances, particularly antidiabetic or hypolipidemic agents that act through mechanisms other than those underlying the effects of the compounds of the invention. Agents which can advantageously be combined with compounds of the invention in a single formulation include but are not limited to biguanides such as metformin, insulin releasing agents such as the sulfonylurea insulin releaser glyburide and other sulfonylurea insulin releasers, cholesterol-lowering drugs such as the "statin" HMG-CoA reductase inhibitors such as atrovastatin, lovastatin, pravastatin and simvastatin, PPAR-alpha agonists such as clofibrate and gemfibrozil, PPAR-gamma agonists such as thiazolidinediones (e.g. rosiglitazone and pioglitazone, alpha-glucosidase inhibitors such as acarbose (which inhibit starch digestion), and prandial insulin releasers such as repaglinide. The amounts of complementary agents combined with compounds of the invention in single formulations are in accord with the doses used in standard clinical practice. Established safe and effective dose ranges for certain representative compounds are set forth above.

The invention will be better understood by reference to the following examples which illustrate but do not limit the invention described herein.

CHEMICAL SYNTHESIS EXAMPLES

Example 1

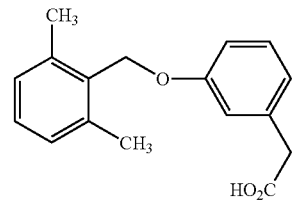

3-(2,6-Dimethylbenzyloxy)phenylacetic acid

Step A: Preparation of Ethyl 3-hydroxyphenylacetate

To a stirred solution of 3-Hydroxyphenylacetic acid (10 g, 65.7 mmol) and 1,3-dicyclohexylcarbodiimide (DCC, 16.27 g, 78.8 mmol) in DMF (30 ml) was added pyridine (2.5 ml) followed by absolute ethanol (15 ml, 255.5 mmol). The reaction mixture was stirred at room temperature for 16 hours, filtered, concentrated and purified by flash chromatography on a silica gel column (hex:ethyl acetate 2:1) to give the title compound.

$^1$H NMR (270 MHz, CDCl$_3$): 1.2 (t, 3H); 3.5 (s, 2H); 4.1 (q, 2H); 6.6-7.2 (m, 4H).

Step B: Preparation of Ethyl 3-(2,6-dimethylbenzyloxy)phenylacetate

A solution of 2,6-Dimethylbenzyl alcohol (5.25 g, 38.6 mmol) and diisopropyl azodicarboxylate (DIAD, 8.49 g, 42 mmol) in THF (30 ml) and DMF (13 ml) was added drop wise to a solution of Ethyl 3-hydroxyphenylacetate (Step A, 6.66 g, 37 mmol) and triphenylphosphine (11 g, 42 mmol) in THF (100 ml). The reaction mixture was stirred at room temperature for 4 hours, diluted with ether and washed with water. The organic layer was dried over Na$_2$SO$_4$, filtered, concentrated, and purified by flash chromatography on a silica gel column (hex:ethyl acetate 1:1) to give the title compound.

$^1$H NMR (270 MHz, CDCl$_3$): 1.2 (t, 3H); 2.4 (s, 6H); 3.5 (s, 2H); 4.1 (q, 2H); 5.1 (s, 2H); 6.9 (m, 2H); 7.15-7.35 (m, 5H).

Step C: Preparation of 3-(2,6-Dimethylbenzyloxy)phenylacetic acid

To a stirred solution of Ethyl 3-(2,6-dimethylbenzyloxy) phenylacetate (Step B, 4 g, 13.6 mmol) in absolute ethanol (30 ml) was added 1N NaOH (20 ml) at room temperature. The reaction mixture was stirred for 3 hours, acidified by 1N HCl, and concentrated. The residue was taken into chloroform and washed with 0.1N HCl, dried over Na$_2$SO$_4$, filtered, concentrated and purified by flash chromatography on a silica gel column (hex:ethyl acetate 1:1) to give the title compound.

$^1$H NMR (270 MHz, CDCl$_3$): 2.4 (s, 6H); 3.65 (s, 2H); 5.1 (s, 2H); 6.9 (m, 2H); 7.15-7.35 (m, 5H).

Example 2

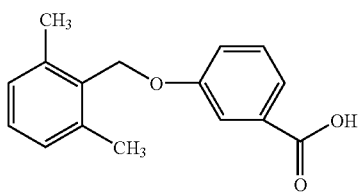

3-(2,6-Dimethylbenzyloxy)benzoic acid

Step A: Preparation of Ethyl 3-(2,6-dimethylbenzyloxy)benzoate

To a stirred solution of Ethyl 3-hydroxybenzoate (12.21 g, 73.47 mmol) and triphenylphosphine (21.01 g, 80.13 mmol) in dry THF (100 ml) was added dropwise a solution of 2,6-Dimethylbenzyl alcohol (10 g, 73.5 mmol) and diisopropyl azodicarboxylate (16.19 g, 80.13 mmol) in dry THF (35 ml) and dry DMF (15 ml) at ambient temperature. After three hours of stirring at room temperature, the reaction mixture was diluted with diethyl ether and washed twice with water and brine. The combined organic layer was dried over Na$_2$SO$_4$, filtered, concentrated and purified by flash chromatography using ethyl acetate:hexane (1:3) as elutent.

$^1$H NMR (270 MHz, CDCl$_3$): 1.4 (t, 3H); 2.4 (s, 6H); 4.4 (q, 2H); 5.1 (s, 2H); 7.1 (m, 2H); 7.2 (m, 2H); 7.4 (t, 1H); 7.9 (m, 2H).

Step B: Preparation of 3-(2,6-Dimethylbenzyloxy)benzoic acid

1N NaOH (86 ml) was added to a stirred solution of Ethyl 3-(2,6-dimethylbenzyloxy)benzoate (Step A, 16.31 g, 57.4 mmol) in absolute alcohol (150 ml). After 3 hours of stirring at room temperature, the reaction mixture was acidified with 1M HCl and concentrated in vacuuo. The organic residue was taken into chloroform and washed with 1N HCl, dried over Na$_2$SO$_4$, filtered, concentrated and purified by flash chromatography using chloroform:methanol (95:5 spiked with acetic acid) as elutent.

$^1$H NMR (270 MHz, CDCl$_3$): 2.4 (s, 6H); 5.1 (s, 2H); 7.15-7.35 (m, 4H); 7.4 (t, 1H); 7.8 (m, 2H).

Example 3

3-(2,6-Dimethylbenzyloxy)benzoic acid

Step A: Mitsunobu Coupling-Ethyl 3-(2,6-dimethylbenzyloxy)benzoate

TABLE 1

| Cpd | hydroxy ester | TPP | THF | benzyl-OH | DIAD | THF | product |
|---|---|---|---|---|---|---|---|
| MW | 166.17 | 262.29 | | 136.19 | 202.21 | | 284.35 |
| Mass | 15.0 | 25.8 | | 12.3 | 19.9 | | |
| Vol | | | 40 | | 19.4 | 40 | |
| Mol | 0.090 | 0.098 | | 0.090 | 0.098 | | |
| D | | | | | 1.027 | | |

Theoretical yield 25.7 g; actual yield 19.85 g; fractional yield 0.773.
Mass = g; vol = mL A solution of ethyl 3-hydroxybenzoate and triphenylphosphine in anhydrous THF was cooled in an ice bath to 5° C. under nitrogen. In a separate flask, a solution of 2,6-dimethylbenzyl alcohol and DIAD in anhydrous THF was prepared and transferred via cannula to first flask. The addition was very exothermic with a rise from 5° C. to 18° C. within the first 2 minutes of the addition (several mLs). The addition was completed over 22 min with a maximum temperature of 24° C. After 30 min of stirring, a precipitate formed and the ice bath was removed. Tlc (hexanes:ether 1:1, UV) after 2.5 h showed a trace of starting material remained.

A variety of solvent systems were used in an attempt to better separate TPP from the product, they included: 10:3 hexanes:ether; 4:1 hexanes:EtOAc; CH$_2$Cl$_2$; 1:1 CH$_2$Cl$_2$; hexanes 10% CH$_2$Cl$_2$ in hexanes; and 5% ether in hexanes. The last solvent system gave the best separation, solvents with CH$_2$Cl$_2$ in ti tended to elute the product and TPP together and quite fast.

TABLE 2

| | tlc data | |
|---|---|---|
| cpd | Rf (H:E 1:1) | Rf (5% E/H) |
| TPP | 0.86 | 0.61 |
| product | 0.75 | 0.27 |
| phenol | 0.49 | 0 |
| BnOH | 0.41 | 0 |
| TPP=O | 0.06 | 0 |

H = hexanes  E = ethyl ether

After 7 h, the reaction mixture was filtered to remove the solids (14.3 g, tlc showed it was TPP oxide) and the filter cake was rinsed with hexanes:ether 1:1 (60 mL). The filtrate was concentrated to give a yellow mixture of oil and solids. This was taken up in 100 mL ether and 100 mL hexanes and allowed to sit for ~1 h. The solids were collected by vacuum filtration (24.0 g, tlc showed only TPP oxide, total solids removed was 38.3 g) and the filtrate was concentrated to give a cream colored solid.

The solid was dissolved in 100 mL $CH_2Cl_2$ and applied to a pad of silica gel (9.5 cm diameter by 6 cm high, ~325 g). This was eluted with $CH_2Cl_2$ and collected into 2×500 mL and 2×250 mL flasks. The product and TPP coeluted into the first 2 flasks and TPP oxide was retained. Concentrated the first 2 fractions to give 23.6 g of white powder. LC/MS (labeled M02130-01) showed 78% pure desired product with 11% TPP as the major impurity.

The crude product was dissolved in ~100 mL ether with heat and allowed to cool. A small amount of solid precipitated. Added 70 g silica gel and concentrated. This was applied to a pad of silica gel (260 g, more than equivalent to a Biotage 75S) and eluted with 1 L 5% ether in hexanes and collected ~200 mL fractions (4 fractions). The first fraction contained TPP and the 4th fraction was almost pure product, the second and third were cross fractions. The silica gel was eluted with 1 L 30% ether in hexanes and collected into 3 fractions. Fractions 5 & 6 had product and were concentrated to give a white solid, 19.85 g (77% yield).

$^1H$ and $^{13}C$ NMR spectra were consistent with the desired product. LC/MS showed M+H=285.1 and 97.7% purity by UV at 250 nm.

$^1H$ NMR (270 MHz, $CDCl_3$): 1.4 (t, 3H); 2.4 (s, 6H); 4.4 (q, 2H); 5.1 (s, 2H); 7.1 (m, 2H); 7.2 (m, 2H); 7.4 (t, 1H); 7.7 (m, 2H).

Step B: Saponification

TABLE 3

| cpd | ester | EtOH | 40% NaOH | water | product |
|---|---|---|---|---|---|
| MW | 284.35 | | 10 N | | 256.30 |
| eq | | | 2.13 | | |
| mass | 10.0 | | | | |

TABLE 3-continued

| cpd | ester | EtOH | 40% NaOH | water | product |
|---|---|---|---|---|---|
| vol | | 250 | 7.5 | 10 | |
| mol | 0.035 | | 0.075 | | |

Theoretical yield 9.01 g; actual yield 5.0 g; fractional yield 0.55

The ester (10 g) from Step A was taken up in 50 mL absolute EtOH. It was not very soluble and addition 50 mL portions of EtOH was added until 250 mL was added. There were still some solids present and heat was applied to form a solution (46° C.). A solution of 7.5 mL 10 N NaOH diluted with 10 mL water was added and the solution was stirred for 1 h. Tlc (hexanes:ether, UV) showed the ester was consumed and an intense spot appeared on the baseline.

Work Up

The reaction was concentrated on a rotary evaporator at 50° C. give a white solid. The solid was slurried in 250 mL deionized water and the insoluble material was collected by filtration. The filtrate was set aside for the time being.

The filter cake was rinsed with 2×200 mL ether and examined by LC/MS after each wash. The purity was 98.4% and 98.7% respectively. The solids were stirred in 200 mL ether for 15 min and collected but filtration. LC/MS showed it was 99.5% pure. The solids were slurried in 100 mL deionized water and treated with 2.5 mL concentrated HCl. A check with pH paper indicated pH1. The slurry was stirred for 22 min and collected by vacuum filtration. The filter cake was rinsed with several portions of water (~100 mL total volume). Dried in vacuo at 45° C. with $P_2O_5$.

$^1H$ NMR spectrum was consistent with the desired product, broad OH centered at ~6 ppm. $^1H$ NMR (270 MHz, $CDCl_3$): 2.4 (s, 6H); 5.1 (s, 2H); 7.1 (m, 2H); 7.15-7.3 (m, 2H); 7.4 (t, 1H); 7.8 (m, 2H).

Example 4

6-[3-(2,6-Dimethylbenzyloxy)-phenyl]-hexanoic acid

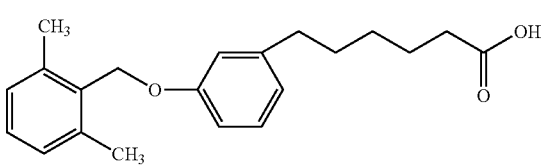

Step A: Synthesis of triphenylethylvalerate phosphonium bromide

TABLE 4

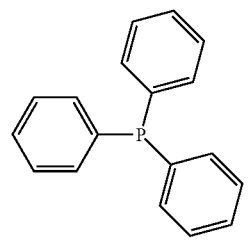

Mol. Wt. 262.29

+

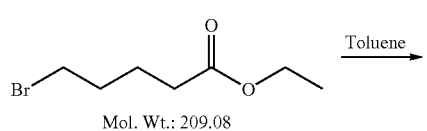

Mol. Wt.: 209.08

→ Toluene

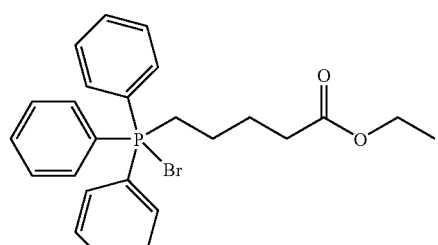

Mol. Wt.: 471.37

| Compound | MW | Moles | grams | ml | Density |
|---|---|---|---|---|---|
| Triphenylphosphine | 262.29 | 0.0450 | 11.80 | | |
| Ethyl-5-bromovalerate | 209.08 | 0.0600 | 12.54 | 9.46 | 1.321 |
| Benzene | 78.02 | | | 25 | |

Dissolved 11.80 g of triphenylphosphine in 25 ml of toluene under nitrogen in a 3-necked, 100 ml round bottom flask equipped with a stir bar, thermocouple and a reflux condenser with a nitrogen inlet. 12.54 g of ethyl-5-bromovalerate was added to the solution, heated to reflux (110° C.) and stirred for 2 hrs. The reaction was analyzed after 1 and 2 hrs. The reaction was cooled to room temperature (<25° C.) and the toluene was decanted away from the oily solid. The residue was slurried in 100 ml of hexanes 3X decanting the hexanes each time. The oily residue was heated on a Kugelrohr apparatus at 40° C., 0.1 Torr for 30 min. to afford 19.0 g (89.6%) of a white oily solid. NMR ($^{32}$P) and NMR ($^{13}$C) showed the desired product.

Step B: Preparation of 6-[3-(2,6 dimethylbenzyloxy)-phenyl]-hex-5-enoic acid ethyl ester

TABLE 5

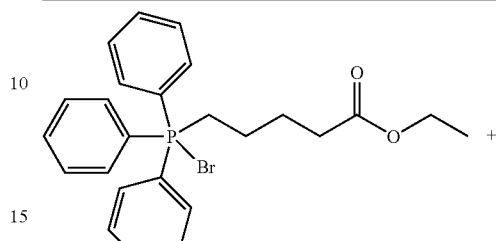

Mol. Wt.: 471.37

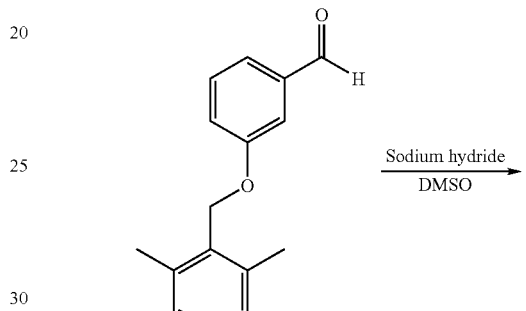

Mol. Wt.: 240.30

→ Sodium hydride / DMSO

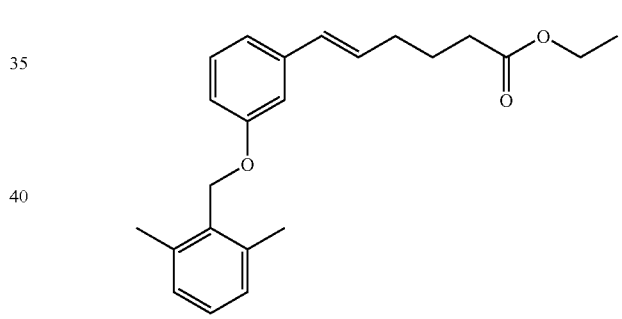

Mol. Wt.: 352.47

| Compound | MW | Moles | grams | Ml |
|---|---|---|---|---|
| Triphenylethyvalerate phosphonium bromide | 471.37 | 0.0282 | 13.29 | |
| 3-(2,6-dimethylbenzyloxy) benzaldehyde | 240.30 | 0.0208 | 5.00 | |
| Sodium hydride | 24.00 | 0.0310 | 0.745 | |
| Dimethyl sulfoxide | 78.13 | | | 40/20 |

A mixture of 13.29 g of triphenylethylvalerate phosphonium bromide and 0.745 g of sodium hydride in 40 ml of DMSO was stirred for 30 min, under nitrogen in a 3-necked, 100 ml round bottom flask equipped with a stir bar, reflux condenser with a nitrogen inlet and a thermocouple. The mixture changed from light yellow to brown and heated to 40.2° C. from 23.2° C. 5.00 g of 3-(2,6-dimethylbenzyloxy) benzaldehyde was dissolved in 20 ml of DMSO and added, dropwise over a 4 min. period to the reaction mixture. The mixture heated to 26.8° C. from 21.8° C. The reaction mixture was stirred and allowed to cool to room temperature. The reaction was analyzed after 1 hr. and LC-MS showed almost all the starting aldehyde left and ~3% desired product. The reaction mixture was heated to 50° C. and stirred for 3 hrs. The reaction was analyzed after 2 and 3 hrs. LC-MS showed ~20% starting aldehyde left and 17% desired product. The reaction was cooled to room temperature and placed in a refrigerator overnight.

The reaction mixture was allowed to warm to room temperature and stirred. A mixture of 5.56 g (118 mM) of triphenylethylvalerate phosphonium bromide and 0.312 g of sodium hydride in 15.0 ml of DMSO was stirred for 30 min. under nitrogen. The mixture was added, in bolus, to the reaction, heated to 50° C. and stirred for 6 hrs.

¹H NMR (270 MHz, CDCl₃): 1.2 (t, 3H); 1.8 (m, 2H); 2.2-2.4 (m, 10H); 4.2 (q, 2H); 5.1 (s, 2H); 5.6-6.2 (m, 1H); 6.4 (t, 1H); 6.9-7.3 (m, 7H).

Step C: Preparation of 6-[3-(2,6-dimethylbenzyloxy)-phenyl]-ethylhexanoate Reference: Journal of Org. Chemistry, Vol. 34, No. 11, p. 3684-85. November 1969

TABLE 6

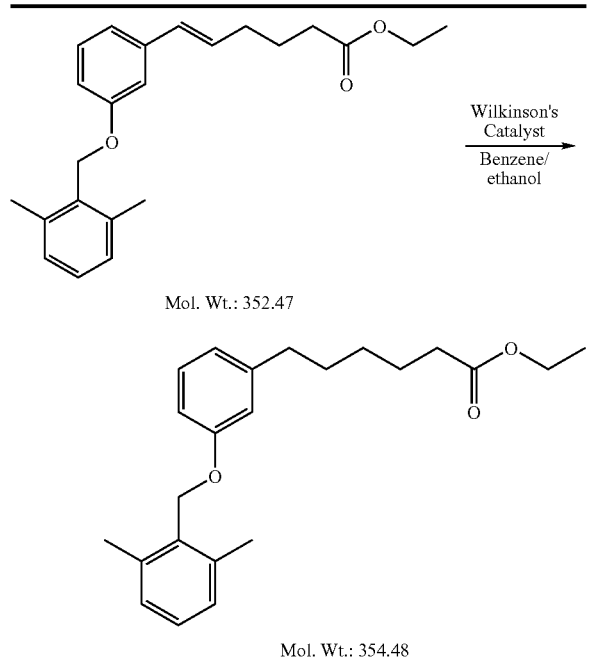

| Compound | MW | mMoles | grams | ml |
|---|---|---|---|---|
| 6-[3-(2,6-dimethylbenzyloxy)-phenyl]-hex-enoic acid ethyl ester | 352.47 | 7.70 | 2.71 | |
| Tris(triphenylphosphine) Chlororhodium (I) | 925.23 | .028 | .0259 | |
| Benzene | 78.11 | | | 60.0 |
| Absolute ethanol | 46.07 | | | 60.0 |

2.71 g of 6-[3{2,6-dimethylbenzyloxy)-phenyl]-hex-5-enoic acid ethyl ester was dissolved in 120 ml of degassed 1:1 mixture of benzene and absolute ethanol in a 300 ml stainless steel Parr pressure reactor. 0.259 g of tris(triphenylphosphine)chlororhodium (I) (Wilkinson's catalyst) was added to the solution. The reaction mixture was sparged 5× with hydrogen, heated to 60° C., 80 psi with hydrogen and stirred overnight.

The reaction was cooled to room temperature and vented. Analysis by LC-MS showed no starting olefin. The reaction solution was sparged with nitrogen and filtered through a bed of celite. The filtrate was concentrated in vacuo to afford 3.40 g of a brown oil. The oil was dissolved in 12 ml of 1:1, hexanes:chloroform. The silica gel was eluted with 100 ml of 1:1, hexanes:chloroform and 200 ml of 95:5, hexanes:ethyl acetate collecting 50 ml fractions. Pure fractions were combined and concentrated in vacuo to afford 2.70 g (99.0%) of a dark yellow oil. LC-MS showed the desired product ~72%. The product was used without further purification.

Step D: Preparation of 6-[3-(2,6-Dimethylbenzyloxy)-phenyl]-hexanoic acid

TABLE 7

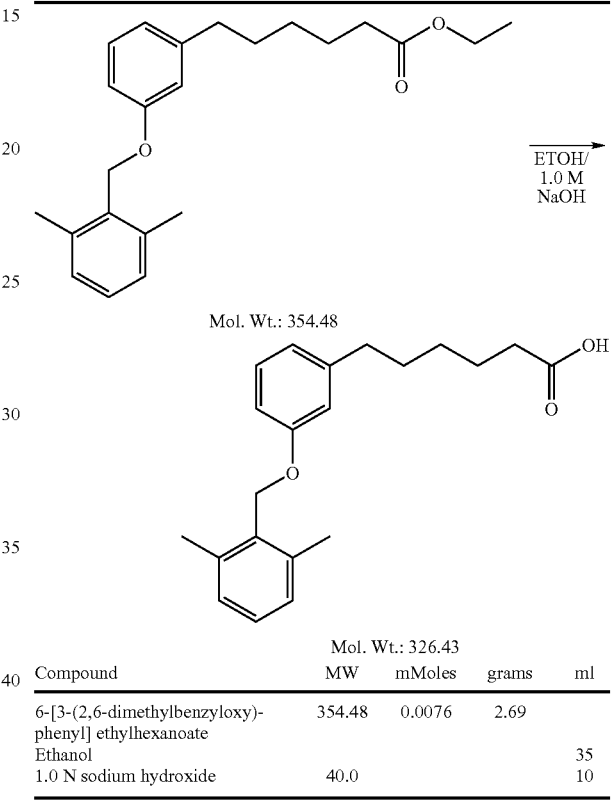

| Compound | MW | mMoles | grams | ml |
|---|---|---|---|---|
| 6-[3-(2,6-dimethylbenzyloxy)-phenyl] ethylhexanoate | 354.48 | 0.0076 | 2.69 | |
| Ethanol | | | | 35 |
| 1.0 N sodium hydroxide | 40.0 | | | 10 |

2.69 g of 6-[3-(2,6-dimethylbenzyloxy)-phenyl]-ethylhexanoate was dissolved in 35 ml of absolute ethanol and 10 ml of 1N aqueous sodium hydroxide in a 100 ml round bottom flask equipped with a stir bar and a reflux condenser. The yellow solution was heated to reflux and stirred for 2 hrs. The reaction was analyzed and LC-MS showed no starting ethyl ester. The reaction was cooled to room temperature and concentrated in vacuo to a yellow oil that mostly solidified on standing. 50 ml of water was added to the residue and stirred 10 min. The aqueous solution was extracted 3× with 50 ml of ethyl acetate. The aqueous layer was acidified with 3 ml of 6N aqueous HCl solution and extracted 3× with 50 ml of ethyl acetate. The combined organic layer was dried over sodium sulfate, filtered and concentrated in vacuo to afford ~2.2 g of a gummy yellow solid. The residue was stirred in 75 ml of water for 30 min. The solids were collected by filtration and dried in a vacuum oven at 40° C. to afford 1.62 g (90.5%) of beige solid. LC-MS and NMR showed the desired product >98%.

¹H NMR (270 MHz, CDCl₃): 1.4 (m, 2H); 1.7 (m, 4H); 2.3-2.4 (m, 8H); 2.6 (t, 2H); 5.0 (s, 2H); 6.8 (m, 3H); 7.0-7.3 (m, 4H).

Example 5

5-[3-(2,6-Dimethylbenzyloxy)-phenyl]pentanoic acid

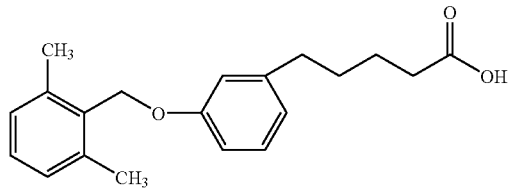

Step A: Preparation of 5-[3-(2,6-dimethylbenzyloxy)-phenyl]-pent-4-enoic acid ethyl ester

TABLE 8

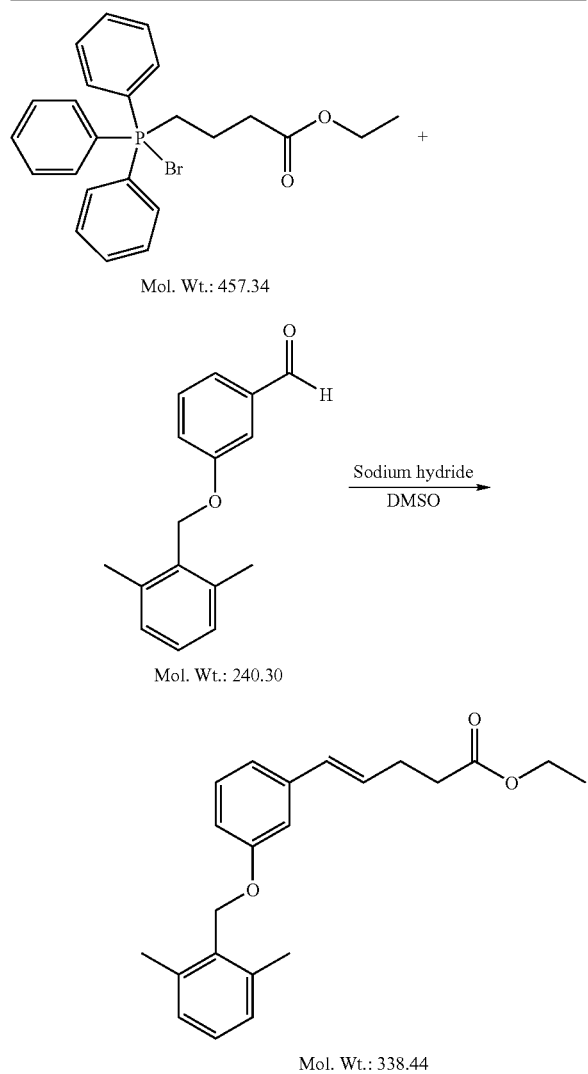

| Compound | MW | Moles | grams | ml |
|---|---|---|---|---|
| Triphenylethylbutyrate phosphonium bromide | 457.34 | 0.0220 | 10.06 | |
| 3-(2,6-dimethylbenzyloxy) benzaldehyde | 240.30 | 0.0162 | 3.89 | |

TABLE 8-continued

| | | | |
|---|---|---|---|
| Sodium hydride | 24.00 | 0.0242 | 0.581 |
| Dimethyl sulfoxide | 78.13 | | | 30.0/15.0 |

A mixture of 10.06 g of triphenylethylbutyrate phosphonium bromide and 0.581 g of sodium hydride in 30.0 ml of DMSO was stirred for 30 min. under nitrogen in a 3-necked, 100 ml round bottom flask equipped with a stir bar, reflux condenser with a nitrogen inlet a thermocouple. The mixture changed from yellow to orange and heated to 26.7° C. from 19.8° C. 3.89 g of 3-(2,6-dimethylbenzyloxy)benzaldehyde was dissolved in 15.0 ml of DMSO and added, dropwise, over a 3 min period of the reaction mixture. The mixture changed from orange to yellow and heated to 34.0° C. from 26.7° C. The reaction mixture was stirred and allowed to cool to room temperature for 3 hrs. The reaction was analyzed after 1 and 3 hrs. LC showed the progress of the reaction from ~15% to ~13% starting aldehyde left. The reaction mixture was heated to 50° C. and stirred for 2 hrs. The reaction was analyzed after 1 and 2 hrs. LC-MS showed little change from the previous samples with ~12% starting aldehyde left. The reaction mixture was cooled to room temperature and placed in a refrigerator overnight.

The reaction mixture was allowed to warm to room temperature and stirred. A mixture of 3.20 g (70 mM) of triphenylethylbutyrate phosphonium bromide and 0.185 g of sodium hydride in 10.0 ml of DMSO was stirred for 30 min. under nitrogen. The mixture was added, in bolus, to the reaction and stirred at room temperature for 2 hrs.

The reaction was analyzed after 1 and 2 hrs. LC showed the progress of the reaction from ~13% to ~4% starting aldehyde left. The reaction mixture was heated to 50° C. and stirred for 2 hrs. The reaction was cooled to room temperature and poured over 50 g of ice with 50 ml of water. The aqueous mixture was extracted 3× with 125 ml of ethyl acetate and the combined organic layer was dried over sodium sulfate, filtered and concentrated in vacuo to afford 12.9 g of a brown oil. LC showed ~40% desired product.

The oil dissolved in 30 ml of 95:5, hexanes:ethyl acetate and chromatographed on a BIOTAGE 75S silica gel column using 5 liters of 95:5, hexanes:ethyl acetate. The desired product eluted quickly, possibly due to residual DMSO from the work up. The fractions containing the desired product were combined and concentrated in vacuo to afford 4.9 g of a yellow oil. The oil was dissolved in 10 ml of 1:1, hexanes: chloroform and placed on 30 g silica gel equilibrated with 1:1, hexanes:chloroform. The silica gel was eluted with 200 ml 1:1, hexanes:chloroform and 200 ml of 9:1, hexanes:ethyl acetate collecting 50 ml fractions. Pure fractions were combined and concentrated in vacuo to afford 3.40 g (62.0%) of a faint yellow oil that mostly solidified upon standing. LC-MS and NMR show the desired product >98% with about a 30:70 cis to trans isomeric ratio based on the Wittig reaction producing predominantly the trans isomer.

$^1$H NMR (270 MHz, CDCl$_3$): 1.2 (t, 3H); 2.4-2.7 (m, 10H); 4.1 (q, 2H); 5.1 (s, 2H); 5.6-6.2 (m, 1H); 6.5 (t, 1H); 6.8 (m, 7H).

Step B: Preparation of 5-[3-(2,6-dimethylbenzyloxy)-phenyl]-ethylpentanoate

Reference: The Journal of Org. Chemistry, Vol. 34, No. 11, p. 3684-85, November 1996

TABLE 9

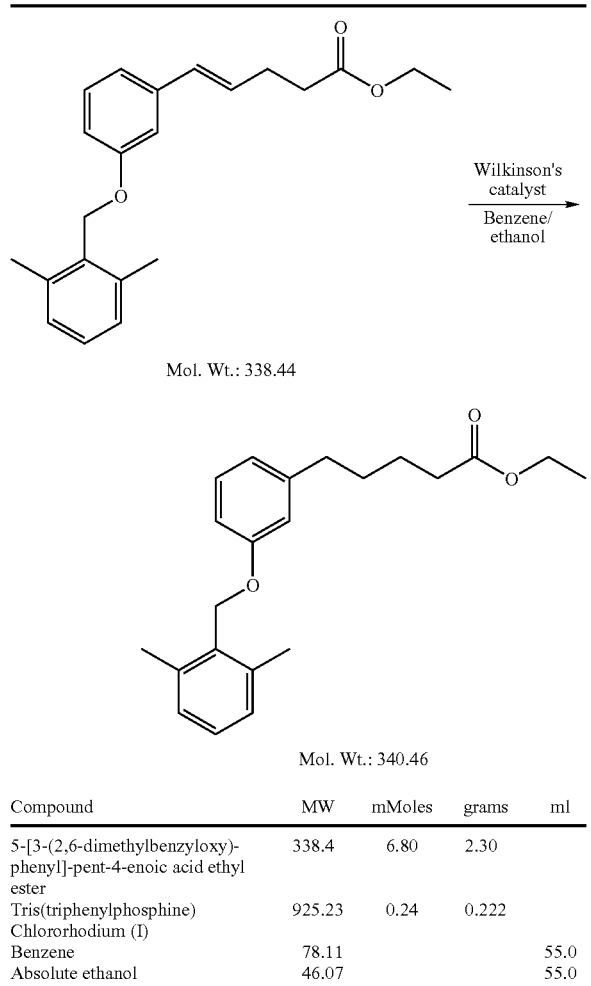

| Compound | MW | mMoles | grams | ml |
|---|---|---|---|---|
| 5-[3-(2,6-dimethylbenzyloxy)-phenyl]-pent-4-enoic acid ethyl ester | 338.4 | 6.80 | 2.30 | |
| Tris(triphenylphosphine) Chlororhodium (I) | 925.23 | 0.24 | 0.222 | |
| Benzene | 78.11 | | | 55.0 |
| Absolute ethanol | 46.07 | | | 55.0 |

2.50 g of 5-[3-(2,6-dimethylbenzyloxy)-phenyl]-pent-4-enoic and acid ethyl ester was dissolved in 110 ml of a degassed 1:1 mixture of benzene and absolute ethanol in a 300 ml stainless steel Parr pressure reactor. 0.222 g of tris (triphenylphosphine)chlororhodium (I) (Wilkinson's catalyst) was added to the solution. The reaction mixture was sparged 5× with hydrogen, heated to 60° C., 80 psi with hydrogen and stirred overnight.

The reaction was cooled to room temperature and vented. Analysis by LC-MS showed no starting olefin. The reaction solution was sparged with nitrogen and filtered through a bed of celite. The filtrate was concentrated in vacuo to afford 3.20 g of a brown oil. The oil was dissolved in 12 ml of 1:1, hexanes:chloroform and placed on 30 g of silica gel equilibrated with 1:1, hexanes:chloroform. The silica gel was eluted with 100 ml of 1:1, hexanes:chloroform and 200 ml of 95:5, hexanes:ethyl acetate collecting 50 ml fractions. Pure fractions were combined and concentrated in vacuo to afford 2.30 g (99.0%) of a faint yellow oil. LC-MS showed the desired product ~93%. The product was used without further purification.

$^1$H NMR (270 MHz, CDCl$_3$): 1 (t, 3H); 1.4 (m, 4H); 2.0 (t, 2H); 2.1 (s, 6H); 2.4 (m, 2H); 3.8 (q, 2H); 4.7 (s, 2H); 6.5 (m, 3H); 6.8-7.0 (m, 4H).

Step C: Preparation of 5-[3-(2,6 dimethylbenzyloxy)-phenyl]-pentanoic acid

TABLE 10

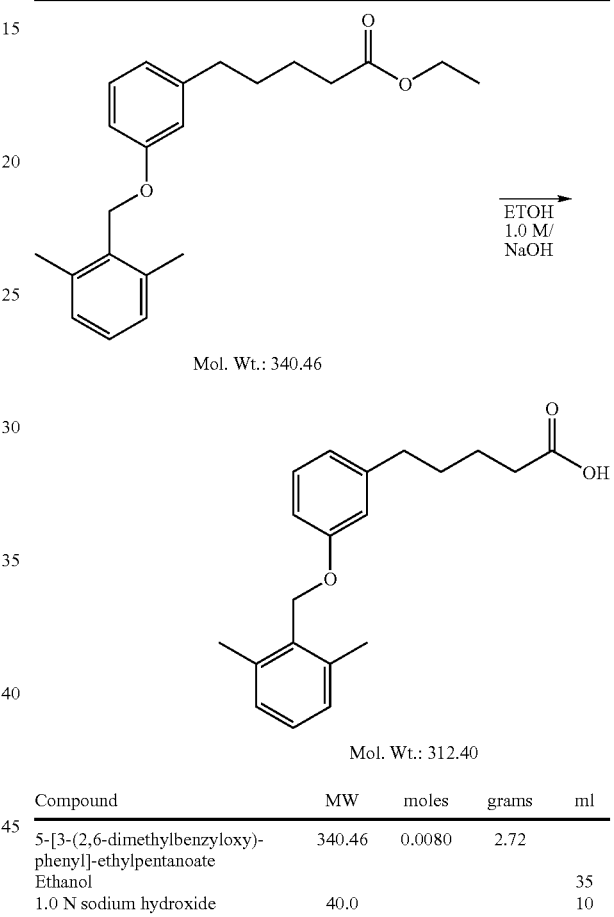

| Compound | MW | moles | grams | ml |
|---|---|---|---|---|
| 5-[3-(2,6-dimethylbenzyloxy)-phenyl]-ethylpentanoate | 340.46 | 0.0080 | 2.72 | |
| Ethanol | | | | 35 |
| 1.0 N sodium hydroxide | 40.0 | | | 10 |

2.72 g of 5-[3-(2,6-dimethylbenzyloxy)-phenyl]-ethylpentanoate was dissolved in 35 ml of absolute ethanol and 10 ml of 1N aqueous sodium hydroxide in a 100 ml round bottom flask equipped with a stir bar and a reflux condenser. The light yellow solution turned was heated to reflux and stirred for 1 hr. The reaction was analyzed and LC-MS showed no starting ethyl ester. The reaction was cooled to room temperature and concentrated in vacuo to a white solid. 50 ml of water was added to dissolve the solid. The aqueous solution was extracted 3× with 50 ml of ethyl acetate. The aqueous layer was acidified with 3 ml of 6N aqueous HCl solution and extracted 3× with 50 ml of ethyl acetate. The combined organic layer was dried over sodium sulfate, filtered and concentrated in vacuo to afford ~2.5 g of a white gummy solid. The solid was stirred in 25 ml of hexanes for 30 min., collected by filtration and dried in a vacuum oven at 40° C. to afford 2.12 g (84.8%) of a white solid. LC-MS and NMR showed the desired product >99%.

$^1$H NMR (270 MHz, CDCl$_3$): 1.7 (m, 4H); 2.4 (m, 8H); 2.6 (m, 2H); 5.0 (s, 2H); 6.8 (m, 3H); 7.0-7.3 (m, 4H).

Example 6

3-[3-(2,6-dimethylbenzyloxy)-phenyl]-propionic acid

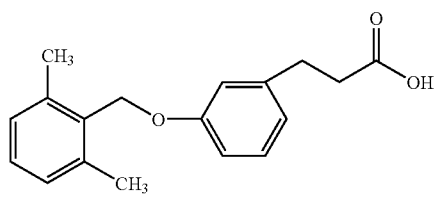

Step A: Synthesis of ethyl-3-hydroxyphenylpropionate

TABLE 11

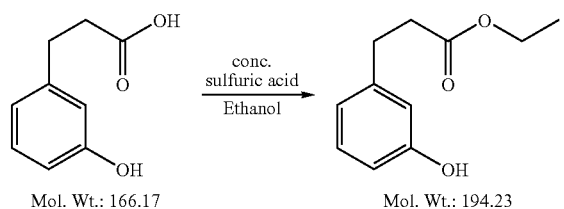

| Compound | MW | moles | grams | ml |
|---|---|---|---|---|
| 3-(3-hydroxyphenyl)-propionic acid | 166.18 | 0.0301 | 5.00 | |
| Ethanol | 46.07 | | | 5.0 |
| Concentrated Sulfuric acid | 96.03 | | | 0.5 |

5.00 g 3-(3-hydroxyphenyl)propionic acid were dissolved in 50 ml of absolute ethanol in a 3-necked, 100 ml round bottom flask equipped with a mechanical stirrer, a reflux condenser and a thermocouple. 0.5 ml of concentrated sulfuric acid were added to the solution and heated to reflux (80° C.) and stirred for 2 hrs. The reaction was analyzed and LC-MS showed the desired product with no starting material. The reaction was cooled to <5° C. in an ice bath and neutralized to pH ~7 with 10 ml of 10% aqueous sodium carbonate solution. The neutralized solution was concentrated in vacuo to ~10 ml and diluted with 25 ml of water. The solution was extracted 3× with 25 ml of ethyl acetate. The combine organic layer was dried over sodium sulfate, filtered and concentrated in vacuo to afford 5.06 g (86.5%) of a dark amber oil. LC-MS and NMR MFG showed the desired product >99.5%.

$^1$H NMR (270 MHz, CDCl$_3$): 1.2 (t, 3H); 2.6 (t, 2H); 2.8 (t, 2H); 4.2 (q, 2H); 6.7-6.8 (m, 3H); 7.2 (m, 1H).

Step B: Synthesis of ethyl-3-(2,6 dimethylbenzyloxy)phenylpropionate

TABLE 12

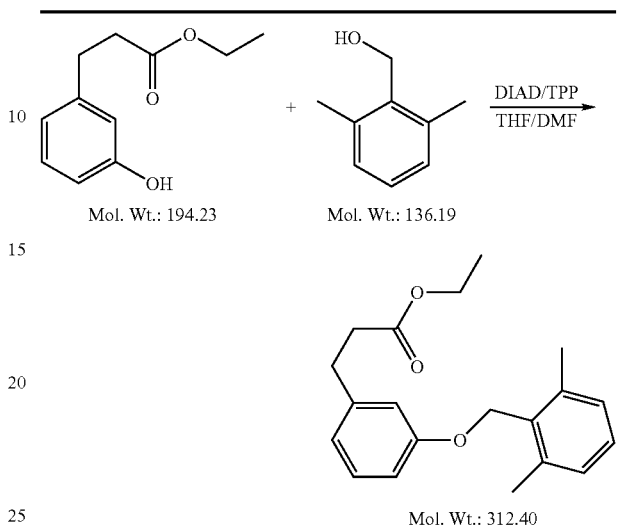

| Compound | MW | moles | grams | ml |
|---|---|---|---|---|
| Ethyl-3-hydroxyphenyl-propionate | 194.23 | 0.0260 | 5.05 | |
| 2,6-dimethylbenzyl alcohol | 136.19 | 0.0271 | 3.69 | |
| Isopropyl azodicarboxylate | 202.21 | 0.0296 | 5.99 | |
| Triphenylphosphine | 262.29 | 0.0296 | 7.76 | |
| Tetrahydofuran | 72.11 | | | 24/76 |

A solution of 3.69 g of 2,6-dimethylbenzyl alcohol and 5.99 g of diisopropyl azodicarboxylate in 24 ml of THF was added, dropwise, to a solution of 5.05 g of ethyl-3-hydroxyphenylpropionate and 7.76 g of triphenylphosphine in 76 ml of THF at such a rate as to keep the reaction temperature <25° C., (Tmax=22.3° C.). The reaction was stirred at room temperature for 4 hrs. in a 3-necked, 250 ml round bottom flask equipped with a stir bar, addition funnel and thermocouple. The reaction was analyzed after 3 and 4 hrs. at room temperature. LC-MS showed mostly desired product with ~4.5% starting material. The reaction was concentrated in vacuo to afford a dark yellow oil. 200 ml hexanes was added to the oil and the solution was stirred in an ice bath (<5° C.) for 1 hr. The solids were collected by filtration and washed 3× with 40 ml of hexanes. The solids were analyzed and NMR showed that they are a mixture of triphenylphosphine oxide and reduced DIAD. LC-MS showed the hexanes filtrate to contain ~58% desired product. The filtrate was concentrated in vacuo to afford 10.2 g of a yellow oil. The oil was dissolved in 5 ml of absolute ethanol 75 ml of hexanes was added and the solution was placed in a freezer overnight. The solids were collected by filtration and dried. NMR showed that 4.3 g of white solids to be ~80%. The solids were combined with the hexanes/ethanol filtrate and concentrated in vacuo to afford 9.3 g of a light yellow oil that was saponified without further purification.

$^1$H NMR (270 MHz, CDCl$_3$): 1.2 (t, 3H); 2.4 (s, 6H); 2.6 (t, 2H); 3.0 (t, 2H); 4.2 (q, 2H); 5.1 (s, 2H); 6.8 (m, 3H); 7.2-7.4 (m, 4H).

Step C: Synthesis of 3-(2,6-dimethylbenzyloxy)phenylpropionic acid

TABLE 13

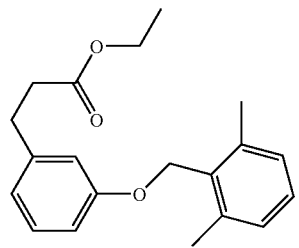

Mol. Wt.: 312.40

Mol. Wt.: 284.35

| Compound | MW | moles | grams | ml |
|---|---|---|---|---|
| Ethyl-3-(2,6-dimethylbenzyloxy)phenylpropionate | 312.40 | | 9.3 | |
| Ethanol | 46.07 | | | 75 |
| 7.5 N sodium hydroxide | 40.0 | | | 4.0 |

9.3 g of an oil containing ~60% ethyl-3-(2,6-dimethylbenzyloxy)phenylpropionate was dissolved in 75 ml of absolute ethanol in a single necked, 250 ml round bottom flask equipped with a stir bar and reflux condenser. 4.0 ml of 7.5N sodium hydroxide was added to the solution. The light yellow solution was heated to reflux (80° C.) and stirred for 1 hr. The reaction was analyzed and LC-MS showed the desired product and no starting ester. The reaction was cooled to room temperature and concentrated in vacuo to afford a yellow oil. The oil was dissolved in 25 ml of water and extracted 3× with 25 ml of ether. The aqueous layer was cooled to <5° C. in an ice bath and acidified to a pH=1 by slowly adding 15 ml of 6N aqueous HCl solution. The precipitated solid were collected by filtration, washed 3X with 25 ml of water and air-dried. The solids were slurried in 100 ml of hexanes and collect by filtration, washed 3× with 25 ml of hexanes and air-dried. LC-MS showed the solids to be ~80% desired product. The solids were heated to 70° C. in 44 ml of 3:1, absolute ethanol:water mixture. The solution was stirred and allowed to cool to room temperature in a tap water bath. The solids were collected by filtration, washed with 20 ml of 3:1, absolute ethanol:water mixture and air-dried. LC-MS showed the solid to be ~98.5% desired product. The solids were heated to 70° C. in 36 ml of 3:1, absolute ethanol:water mixture. The solution was stirred and allowed to cool to room temperature in a tap water bath. The solids were collected by filtration, washed with 20 ml of a 3:1, absolute ethanol:water mixture and air-dried. LC-MS and NMR showed the solids to be >99.5% desired product. The white solid was dried in a vacuum oven at 40° C. for 2 hrs. to afford 3.91 g (52.9%).

$^1$H NMR (270 MHz, CDCl$_3$): 2.4 (s, 6H); 2.2 (m, 2H); 3.0 (m, 2H); 5.1 (s, 2H); 6.8 (m, 3H); 7.1-7.3 (m, 4H).

BIOLOGICAL ACTIVITY EXAMPLES

For all of the biological activity examples that follow, Compound CF was produced in accordance with chemical synthesis example 1. For the in vivo activity experiments Compound CG was produced in accordance with synthesis example 3. For the in vitro activity experiments Compound CG was produced in accordance with synthesis example 2.

Example A

Antidiabetic effects in ob/ob mice

Obese (ob/ob) mice have a defect in the protein leptin, a regulator of appetite and fuel metabolism, leading to hyperphagia, obesity and diabetes.

Male obese (ob/ob homozygote) C57BL/6J mice, approximately 8 weeks of age, were obtained from Jackson Labs (Bar Harbor, Me.) and randomly assigned into groups of 5 animals each such that the body weights (45-50 g) and serum glucose levels ($\geq$300 mg/dl in fed state) were similar between groups. A minimum of 7 days was allowed for adaptation after arrival. All animals were maintained under controlled temperature (23° C.), relative humidity (50+5%) and light (7:00-19:00), and allowed free access to standard chow (Formulab Diet 5020 Quality Lab Products, Elkridge, Md.) and water.

Treatment cohorts were given daily oral doses of vehicle (1% hydroxypropyl-methylcellulose), Compounds BI, CF, CA, CB, CC, or CD for 2 weeks. At the end of the treatment period 100 µt of venous blood was withdrawn in a heparinized capillary tube from the retro-orbital sinus of ob/ob mice for serum chemistry analysis.

After 2 weeks of daily oral dosing, Compound BI (100 mg/kg) and Compound CF (60 mg/kg) elicited a significant reduction in blood glucose (Table 14), triglycerides and free fatty acids (Table 15) as described below.

TABLE 14

Effects of Compounds BI, CF, CA, CB, CC, and CD in the male ob/ob mouse model of Type II diabetes

| Groups | Glucose mg/dL | Glucose (% of Control) |
|---|---|---|
| Vehicle (Control) | 423.6 ± 55.0 | 100.0 ± 13.0 |
| BI - 30 mg/kg | 301.4 ± 29.0 | 71.0 ± 7.0 |
| BI - 60 mg/kg | 248.8 ± 20.0 | 59.0 ± 5.0* |
| BI - 100 mg/kg | 196.3 ± 6.0 | 46.0 ± 1.0* |
| CF - 60 mg/kg | 161.2 ± 14.0 | 38.0 ± 3.0* |
| CA - 60 mg/kg | 402.6 ± 61.0 | 95 ± 14.0 |
| CB - 60 mg/kg | 494.4 ± 72.3 | 117.0 ± 17.0 |
| CC - 60 mg/kg | 444.4 ± 89.5 | 105.0 ± 21.0 |
| CD - 60 mg/kg | 505.6 ± 63.5 | 119.0 ± 15.0 |

*$p < 0.05$ significantly different compared with vehicle-control

TABLE 15

Effects of Compounds BI, CF, CA, CB, CC, and CD on plasma serum glucose, triglycerides, and free fatty acids in obese (ob/ob) mice

| Group | Glucose ± SEM | Triglycerides ± SEM | Free Fatty Acids ± SEM |
|---|---|---|---|
| Vehicle | 423.6 ± 55.0 | 121.8 ± 29.4 | 1612.4 ± 169.7 |
| BI - 30 mg/kg | 301.4 ± 29.0 | 66.6 ± 3.6 | 1272.8 ± 32.5 |
| BI - 60 mg/kg | 248.8 ± 20.0 | 61.4 ± 3.6 | 1168.6 ± 56.7 |

TABLE 15-continued

Effects of Compounds BI, CF, CA, CB, CC, and CD on plasma serum glucose, triglycerides, and free fatty acids in obese (ob/ob) mice

| Group | Glucose ± SEM | Triglycerides ± SEM | Free Fatty Acids ± SEM |
|---|---|---|---|
| BI - 100 mg/kg | 196.3 ± 6.0 | 55.0 ± 3.4 | 1245.4 ± 20.0 |
| BI - 60 mg/kg | 161.2 ± 14.0 | 53.8 ± 1.5 | 1081.6 ± 47.7 |
| CA - 60 mg/kg | 402.6 ± 61.0 | 92.6 ± 13.7 | 1572.2 ± 118.0 |
| CB - 60 mg/kg | 494.4 ± 72.3 | 118.8 ± 18.0 | 2076.2 ± 169.0 |
| CC - 60 mg/kg | 444.4 ± 89.5 | 91.6 ± 13.4 | 2043.6. ± 285.0 |
| CD - 60 mg/kg | 505.6 ± 63.5 | 119.0 ± 14.2 | 1961.8 ± 194.2 |

Example B

Antidiabetic effects in db/db mice db/db mice have a defect in leptin signaling, leading to hyperphagia, obesity and diabetes. Moreover, unlike ob/ob mice on a C57BL/6J background, db/db mice on a C57BL/KS background undergo failure of their insulin-producing pancreatic islet cells, resulting in progression from hyperinsulinemia (associated with peripheral insulin resistance) to hypoinsulinemic diabetes.

Male obese (db/db homozygote) C57BL/Ksola mice approximately 8 weeks of age, were obtained from Jackson Labs (Bar Harbor, Me.) and randomly assigned into groups of 5-7 animals such that the body weights (50-55 g) and serum glucose levels ($\geq$300 mg/dl in fed state) were similar between groups; male lean (db/+heterozygote) mice served as cohort controls. A minimum of 7 days was allowed for adaptation after arrival. All animals were maintained under controlled temperature (23° C.), relative humidity (50±5%) and light (7:00-19:00), and allowed free access to standard chow (Formulab Diet 5008, Quality Lab Products, Elkridge, Md.) and water.

Treatment cohorts were given daily oral doses of Vehicle (1% hydroxypropylmethylcellulose), Compounds BI, CE, BT, BV, BV or Fenofibrate for 2 weeks. At the end of the treatment period 100 pt of venous blood was withdrawn in a heparinized capillary tube from the retro-orbital sinus of db/db mice for serum chemistry analysis.

Effects of compounds of the invention on nonfasting blood glucose are shown in Table 16; effects on serum triglycerides and free fatty acids are shown in Table 17.

TABLE 16

The effects of Compounds BI, CE, BT, BU, BV and fenofibrate in db/db mice

| Groups | Glucose mg/dL | Glucose (% of Control) |
|---|---|---|
| Vehicle (Control) | 692.5 ± 55.4 | 100 ± 8 |
| BI - 100 mg/kg | 347.0 ± 43.1* | 50 ± 6* |
| CE - 93 mg/kg | 372.0 ± 53.8* | 54 ± 8* |
| BT - 107 mg/kg | 684.3 ± 63.6 | 99 ± 9 |
| BU - 128 mg/kg | 533.3 ± 46.7 | 77 ± 7 |
| BV - 115 mg/kg | 789.5 ± 38.9 | 114 ± 6 |
| Fenofibrate - 113 mg/kg | 563.2 ± 49.0 | 81 ± 7 |

Blood glucose levels in lean, nondiabetic db/+ heterozygote mice were 208.5 ± 6.6 mg/dL

TABLE 17

Effect of Compounds BI, CE, BT, BU, BV and Fenofibrate on serum triglycerides and free fatty acids in db/db mice

| Group | Triglycerides ± SEM (mg/dL | Free Fatty Acids ± SEM (μM) |
|---|---|---|
| Lean | 114.2 ± 8.7 | 2315.8 ± 238.3 |
| Vehicle | 232.8 ± 20.7 | 3511.8 ± 257.6 |
| BI | 77.8 ± 5.3 | 1997.2 ± 196.4 |
| CE | 132.0 ± 15.2 | 2867.4 ± 267.7 |
| BT | 211.5 ± 21.5 | 3897.7 ± 291.3 |
| BU | 172.5 ± 9.9 | 3587.0 ± 156.3 |
| BV | 153.2 ± 14.2 | 3373.8 ± 233.6 |
| Fenofibrate | 109.3 ± 9.1 | 3318.5 ± 208.7 |

Example C

Antidiabetic effects in db/db mice

C57BL/Ksola (db/db) mice have a defect in leptin signaling, leading to hyperphagia, obesity and diabetes. Moreover, unlike ob/ob mice on a C57BL/6J background, db/db mice on a C57BLKS background undergo failure of their insulin-producing pancreatic islet cells, resulting in progression from hyperinsulinemia (associated with peripheral insulin 12 resistance) to hypoinsulinemic diabetes.

Male obese (db/db homozygote) C57BL/Ksola mice approximately 8 weeks of age, were obtained from Jackson Labs (Bar Harbor, Me.) and sorted into groups of 7 animals each animals such that the body weights (40-45 g) and serum glucose levels ($\geq$300 mg/dl in fed state) were similar between groups. A minimum of 7 days was allowed for adaptation after 18 arrival. All animals were maintained under controlled temperature (23° C.), relative humidity (50±5%) and light (7:00-19:00), and allowed free access to standard chow (Formulab Diet 5008, Quality Lab Products, Elkridge, Md.) and water.

Treatment cohorts were given daily oral doses of vehicle (1% hydroxypropylmethylcellulose), Compounds BI, CF, CG, or phenylacetate for 17 days. At the end of the treatment period, blood samples were collected and serum glucose and triglycerides were measured. A statistically significant reduction in blood glucose or triglycerides versus animals treated with oral vehicle is considered a positive screening result for a drug.

TABLE 18

The effects of Compounds BI, CF, CG, and phenylacetate in a db/db mouse model of type I diabetes

| Groups | Glucose mg/dL (±SEM) | Triglycerides (mg/dL) |
|---|---|---|
| Vehicle (Control) | 812 ± 34 | 352 ± 27 |
| BI - 100 mg/kg | 472 ± 54 | 116 ± 4 |
| BI - 150 mg/kg | 348 ± 67 | 90 ± 6 |
| CF - 30 mg/kg | 586 ± 31 | 156 ± 20 |
| CF - 60 mg/kg | 604 ± 36 | 120 ± 13 |
| CF - 100 mg/kg | 391 ± 61 | 92 ± 6 |
| CG - 100 mg/kg | 753 ± 24 | 166 ± 14 |
| Phenylacetate - 300 mg/kg | 661 ± 64 | 171 ± 33 |

*p < 0.05 significantly different compared with vehicle-control

Example D

Transcription Activation potential of compounds on human and mouse PPARα and PPARβ

Materials and Methods:

Cells were seeded in 24 well plates the day prior to transfection at $5\times10^4$–$2\times10^5$ cells/well, depending upon cell type. Cells were transfected using Lipofectamine 2000 reagent from Invitrogen. A total of 0.8 μg DNA/well was added to 50 μL of Optimem Reduced Serum media (serum free; Gibco). Lipofectamine 2000 was added (2.5 μL/well) to another tube containing 50 μL of Optimem media. Plasmid DNA was added at a ratio of 4:3 (reporter:activator); where appropriate, salmon sperm DNA was substituted for activator expressing plasmid. The reporter plasmid used was pFR-Luc, which has the firefly luciferase gene under the control of a GAL4 UAS (STRATAGENE) containing promoter. The activator expressing plasmids contain yeast GAL4 DNA binding domain (dbd) fusion of either human PPARα ligand binding domain (LBD; a.a. 167-468) or human PPARβ LBD (a.a. 176-479). DNA constructs containing the mouse PPARα or PPARβ LBD fused to the GAL4 DNA binding domain were also used. The two solutions were incubated at room temperature for 5 min, and then combined. The combined solution was incubated at room temperature for approximately 30 min. Cells were washed once with PBS, and 100 μL of transfection mix added to each well. Plates were incubated at 37° C. in a 5% $CO_2$ incubator for 4.5 hr, followed by aspiration of the transfection mix, with plates refed using EMEM complete media (supplemented with 10% FBS, 1X glutamine). 24 hr post-transfection, plates were treated with the appropriate compounds in EMEM complete media, followed by washing once with PBS and addition of 100 μL 1X reporter lysis buffer/well (Promega) 24 hr after treatment. Plates went through one freeze/thaw cycle prior to analysis. Approximately 10 μL of lysate was added to 100 μL of firefly luciferase substrate, mixed by pipetting, and analyzed on a luminometer for 10s using the integration function (relative 12 luciferase units/RLU) or on a Microbeta Trilux (luciferase counts per second/LCPS). Each treatment was performed in triplicate, and in multiple, separate experiments.

Results:

TABLE 19

Mouse PPARγ LBD fusion protein: transcription activation potential in Hepa1.6 cells (mouse hepatoma cell line). Values are in relative luciferase units (RLU) ± standard deviation.

|  | controls | BI | CF |
|---|---|---|---|
| No treatment | 208 ± 38 | Na | na |
| 3 μM rosi | 1817 ± 331 | Na | na |
| 1 μM | na | 210 ± 51 | 361 ± 138 |
| 3 μM | na | 256 ± 33 | 602 ± 144 |
| 5 μM | na | 254 ± 81 | 710 ± 87 |
| 7 μM | na | 265 ± 61 | 786 ± 418 |
| 10 μM | na | 355 ± 53 | 1140 ± 111 |
| 30 μM | na | 441 ± 203 | 1253 ± 554 |
| 100 μM | na | 820 ± 353 | 1534 ± 608 | na = not applicable; nd = not done

TABLE 20a AND 20b

Mouse PPARα and PPARγ LBD fusion proteins: transcription activation potential in C3A cells (human hepatoma cell line). Values are in luciferase counts per second (LCPS) ± standard deviation.

20a. Mouse PPARα.

|  | Wy/control | BI | CE | CF | CG |
|---|---|---|---|---|---|
| Reporter | 8.73 ± 1.85 | na | na | na | na |
| No treatment | 20.27 ± 2.61 | na | na | na | na |
| 1 μM | 406.73 ± 80.11 | 14.67 ± 1.08 | 9.47 ± 2.14 | 13.17 ± 7.84 | 4.43 ± 2.25 |
| 3 μM | 295.8 ± 40.31 | 15.2 ± 2.78 | 9.57 ± 2.61 | 5.63 ± 0.42 | 9.17 ± 3.72 |
| 10 μM | 324.37 ± 11.06 | 15.1 ± 3.78 | 1.17 ± 2.49 | 153.15 ± 24.4 | 7.87 ± 0.7 |
| 30 μM | 414 ± 122.52 | 10.43 ± 1.81 | 7.4 ± 0.23 | 358.6 ± 5.23 | 11.63 ± 5.01 |
| 100 μM | 325.3 ± 91.83 | 15.37 ± 6.21 | 6.13 ± 0.17 | 201.5 ± 50.84 | 11.8 ± 8.95 |
| 200 μM | 115.2 ± 21.52 | 18.6 ± 11.66 | 8 ± 1.88 | 106.77 ± 32.53 | 80.3 ± 2 |

20b. Mouse PPARγ.

|  | Rosiglitazone | BI | CE | CF | CG |
|---|---|---|---|---|---|
| Reporter | 8.73 ± 1.85 | na | na | na | na |
| No treatment | 8.03 ± 1.82 | na | na | na | na |
| 1 μM | 196.8 ± 138.9 | 2.4 ± 2.26 | 14.3 ± 4.5 | 0.33 ± 0.21 | 8.47 ± 5.01 |
| 3 μM | 60.1 ± 29.14 | 2.6 ± 1.41 | 13.43 ± 8.5 | 10.6 ± 8.74 | 14.8 ± 4.3 |
| 10 μM | 432.7 ± 137.4 | 2.2 ± 1.57 | 6.03 ± 3.75 | 17.2 ± 21 | 20.87 ± 4.1 |
| 30 μM | 378 ± 274.5 | 4.9 ± 4.42 | 9.6 ± 5.46 | 88.2 ± 33.2 | 55.4 ± 30.6 |
| 100 μM | 308.6 ± 110.1 | 2.63 ± 1.96 | 11.7 ± 11.7 | 45.8 ± 36.9 | 78.8 ± 23.1 |
| 200 μM | Nd | 65.77 ± 10.55 | 10.5 ± 9.2 | 93.6 ± 29.7 | 101.2 ± 59.1 | na = not applicable; nd = not done

Note:

The concentrations listed in the preceding table are for the test compounds. The concentration of rosiglitazone was one-fifth the test compound concentration; thus 1 μM test compound was compared against 0.2 μM rosiglitzaone, etc.

TABLE 21

Mouse PPARα and PPARγ LBD fusion proteins: transcription activation potential in C3A cells. Values are in RLU ± standard deviation.

21a. Mouse PPARα.

|  | controls | CF | CG |
|---|---|---|---|
| Reporter only | 2259 ± 300 | na | na |
| No treatment | 1217 ± 161 | na | na |
| 100 μM Wy | 55972 ± 5162 | na | na |
| 100 μM fenoprofen | 4440 ± 213 | na | na |
| 100 μM BI | 4421 ± 118 | na | na |
| 1 μM | Na | 2694 ± 159 | 361 ± 398 |
| 3 μM | Na | 4527 ± 740 | 706 ± 399 |
| 5 μM | Na | 7188 ± 1753 | 492 ± 160 |
| 7 μM | Na | 14325 ± 1032 | 652 ± 190 |
| 10 μM | Na | 16680 ± 2432 | 394 ± 84 |
| 30 μM | Na | 38105 ± 3133 | 651 ± 643 |
| 100 μM | Na | 41037 ± 5401 | 926 ± 1362 |

21b. Mouse PPARγ.

|  | controls | BI | CF | CG |
|---|---|---|---|---|
| No treatment | 302 ± 119 | na | na | na |
| 3 μM rosi | 17264 ± 8260 | na | na | na |
| 1 μM | na | 746 ± 362 | 146 ± 119 | 634 ± 195 |
| 3 μM | na | 174 ± 153 | 579 ± 557 | nd |
| 5 μM | na | 996 ± 855 | 476 ± 527 | nd |
| 7 μM | na | 220 ± 137 | 834 ± 984 | nd |
| 10 μM | na | 479 ± 353 | 207 ± 107 | 405 ± 318 |
| 30 μM | na | 557 ± 639 | 818 ± 1201 | 1562 ± 354 |
| 100 μM | na | 3330 ± 1848 | 237 ± 216 | 2555 ± 1609 | na = not applicable; nd = not done

TABLE 22

Human PPARα and PPARγ LBD fusion proteins: transcription activation potential in C3A cells. Values are in LCPS ± standard deviation.

22a. Human PPARα.

|  | Wy | BI | CF | CE | CG |
|---|---|---|---|---|---|
| Reporter | 21.93 ± 6.0 | na | na | na | na |
| No treatment | 180.8 ± 32.2 | na | na | na | na |
| 1 μM | 181.8 ± 47.6 | 127.7 ± 7.1 | 37 ± 11.5 | 14.7 ± 14.6 | 10.9 ± 11.6 |
| 3 μM | 153.1 ± 2.8 | 128 ± 70.7 | 47 ± 22.8 | 13.2 ± 5.8 | 19.1 ± 6.1 |
| 10 μM | 315.4 ± 36.5 | 52.7 ± 8.2 | 19.9 ± 7.8 | 26.2 ± 1.4 | 17.9 ± 5.2 |
| 30 μM | 648.6 ± 47.5 | 55.4 ± 16.2 | 40.2 ± 18.9 | 10.67 ± 1.2 | 38.2 ± 21.1 |
| 100 μM | 412.23 ± 114 | 20.9 ± 13.1 | 19 ± 14.2 | 6.33 ± 2.6 | 23.9 ± 5.3 |
| 200 μM | nd | 31.1 ± 29.4 | 12.9 ± 8.3 | 12.8 ± 3.7 | 159.4 ± 29.6 |

22b. Human PPARγ.

|  | Rosiglitazone | BI | CE | CF | CG |
|---|---|---|---|---|---|
| Reporter | 21.9 ± 6.1 | na | na | na | na |
| No treatment | 39.9 ± 17.5 | na | na | na | na |
| 1 μM | 124 ± 33.8 | 43.3 ± 11.6 | 60 ± 11.6 | 6.2 ± 0.6 | 47.9 ± 7.2 |
| 3 μM | 134.8 ± 47.8 | 26 ± 4.5 | 73.3 ± 30.9 | 49.4 ± 7.8 | 73.6 ± 39.1 |
| 10 μM | 626.6 ± 227 | 40.1 ± 13.5 | 57.3 ± 22.6 | 141.5 ± 25.9 | 72.5 ± 28.2 |
| 30 μM | 887.2 ± 338.2 | 22.9 ± 10.3 | 28.5 ± 16.4 | 230.4 ± 97.2 | 205.6 ± 37.1 |
| 100 μM | 1034.1 ± 400.5 | 34.6 ± 15.6 | 37.7 ± 23.4 | 225.2 ± 57.5 | 403.6 ± 86.1 |
| 200 μM | Nd | 227.3 ± 25.8 | 12.3 ± 4.8 | 280.1 ± 89.7 | 598.1 ± 190.4 | na = not applicable; nd = not done
Note:
The concentrations listed in the preceding table are for the test compounds. The concentration of rosiglitazone was one-fifth the test compound concentration; thus 1 μM test compound was compared against 0.2 μM rosiglitzaone, etc.

What is claimed is:

1. A method for treating a mammalian subject with a condition selected from the group consisting of insulin resistance syndrome, Type II diabetes, and hyperlipidemia, comprising administering to the subject an amount of a biologically active agent effective to treat the condition, wherein the agent is a compound of the formula:

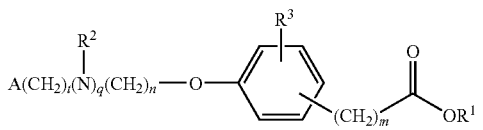

wherein
n is 1 or 2;
m is 1, 2, 4, or 5;
q is 0 or 1;
t is 0 or 1;
$R^2$ is alkyl having from 1 to 3 carbon atoms;
$R^3$ is hydrogen, halo, alkyl having from 1 to 3 carbon atoms, or alkoxy having from 1 to 3 carbon atoms;
A is 2,6-dimethyiphenyl; and
$R^1$ is hydrogen or alkyl having 1 or 2 carbon atoms;
or when $R^1$ is hydrogen, a pharmaceutically acceptable salt of the compound.

2. The method of claim 1, wherein n is 1; q is 0; t is 0; and $R^3$ is hydrogen.

3. The method of claim 1, wherein the subject is a human.

4. The method of claim 3, wherein the agent is administered orally in an amount from one milligram to four hundred milligrams per day.

5. The method of claim 1, wherein the condition is insulin resistance syndrome or Type II Diabetes.

6. The method of claim 2 wherein the biologically active agent is selected from the group consisting of:
3-(2,6-Dimethylbenzyloxy)phenylacetic acid;
6-[3-(2,6-Dimethylbenzyloxy)-phenyl]-hexanoic acid;
Ethyl 6-[3-(2,6-dimethylbenzyloxy)-phenyl]-hexanoate;
5-[3-(2,6-Dimethylbenzyloxy)-phenyl]-pentanoic acid;
Ethyl 5-[3-(2,6-dimethylbenzyloxy)-phenyl]-pentanoate;
3-[3-(2,6-dimethylbenzyloxy)phenyl]-propionic acid; and
Ethyl 3-[3-(2,6-dimethylbenzyloxy)phenyl]-propanoate.

7. The method of claim 6, wherein the biologically active agent is 3-(2,6-Dimethylbenzyloxy)phenylacetic acid.

* * * * *

UNITED STATES PATENT AND TRADEMARK OFFICE
CERTIFICATE OF CORRECTION

PATENT NO. : 7,605,181 B2  Page 1 of 1
APPLICATION NO. : 11/841489
DATED : October 20, 2009
INVENTOR(S) : Kirvin L. Hodge et al.

It is certified that error appears in the above-identified patent and that said Letters Patent is hereby corrected as shown below:

Column 48, line 25 (Claim 1, line 16), change "2,6-dimethyiphenyl" to --2,6-dimethylphenyl--.

Signed and Sealed this

First Day of December, 2009

David J. Kappos
*Director of the United States Patent and Trademark Office*

UNITED STATES PATENT AND TRADEMARK OFFICE
CERTIFICATE OF CORRECTION

PATENT NO. : 7,605,181 B2
APPLICATION NO. : 11/841489
DATED : October 20, 2009
INVENTOR(S) : Kirvin L. Hodge et al.

It is certified that error appears in the above-identified patent and that said Letters Patent is hereby corrected as shown below:

Column 48, line 10 change the chemical structure to the following below.

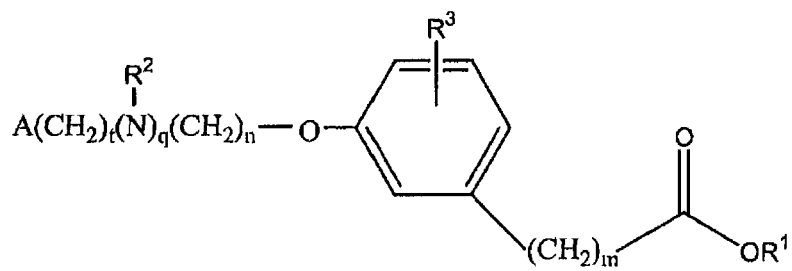

Signed and Sealed this

Seventh Day of December, 2010

David J. Kappos
*Director of the United States Patent and Trademark Office*